United States Patent [19]
Doi et al.

[11] Patent Number: 5,873,824
[45] Date of Patent: Feb. 23, 1999

[54] APPARATUS AND METHOD FOR COMPUTERIZED ANALYSIS OF INTERSTITIAL INFILTRATES IN CHEST IMAGES USING ARTIFICIAL NEURAL NETWORKS

[75] Inventors: Kunio Doi, Willowbrook; Takayuki Ishida, Westmont; Shigehiki Katsuragwa, Chicago, all of Ill.

[73] Assignee: Arch Development Corporation, Chicago, Ill.

[21] Appl. No.: 758,438

[22] Filed: Nov. 29, 1996

[51] Int. Cl.$^6$ .................................................... A61B 5/00
[52] U.S. Cl. .................. 600/408; 600/425; 128/925; 382/132; 382/156; 382/158; 706/20
[58] Field of Search .................... 600/408, 425, 600/410; 128/925; 382/131, 132, 156–159; 395/21, 924; 706/15, 20, 16

[56] References Cited

U.S. PATENT DOCUMENTS 5,491,627  2/1996  Zhang et al. ............................ 600/408
5,622,171  4/1997  Asada et al. ............................ 600/408

*Primary Examiner*—Ruth S. Smith
*Attorney, Agent, or Firm*—Oblon, Spivak, McClelland, Maier & Neustadt, P.C.

[57] ABSTRACT

An automated computer-aided diagnosis (CAD) method and system using artificial neural networks (ANNs) for the quantitative analysis of image data. Three separate ANNs were applied for detection of interstitial disease on digitized two-dimensional chest images. The first ANN was trained with horizontal profiles in regions of interest (ROIs) selected from normal and abnormal chest radiographs. The second ANN was trained using vertical output patterns obtained from the $1^{st}$ ANN for each ROI. The output value of the $2^{nd}$ ANN was used to distinguish between normal and abnormal ROIS with interstitial infiltrates. If the ratio of the number of abnormal ROIs to the total number of all ROIs in a chest image was greater than a certain threshold level, the chest image was considered abnormal. In addition, the third ANN was applied to distinguish between normal and abnormal chest images where the chest image was not clearly normal or abnormal. The ANN trained with image data learns some statistical properties associated with interstitial infiltrates in chest radiographs. In addition, the same technique can be applied to higher-dimensional data (e.g., three-dimensional data and four-dimensional data including time-varying three-dimensional data).

27 Claims, 29 Drawing Sheets

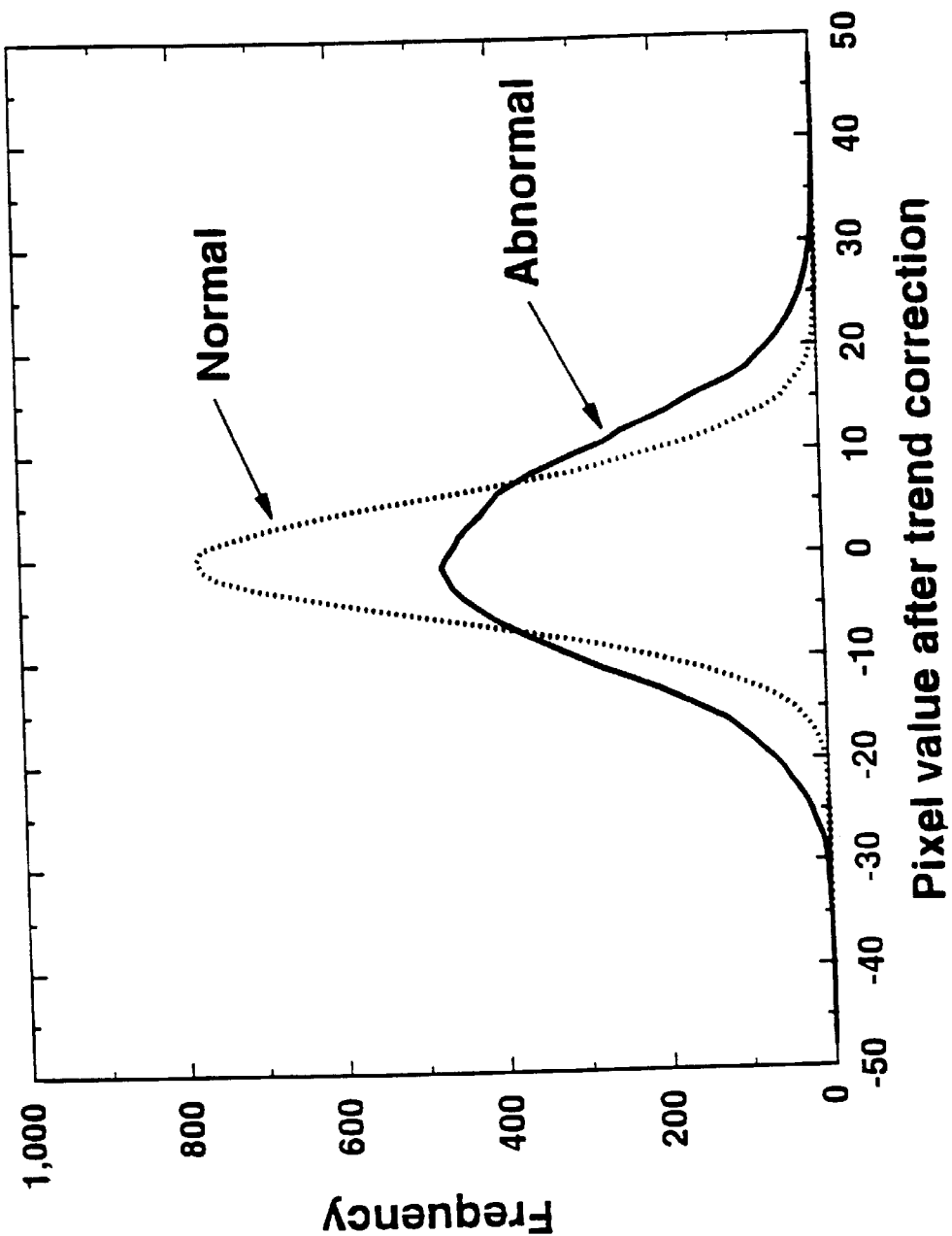

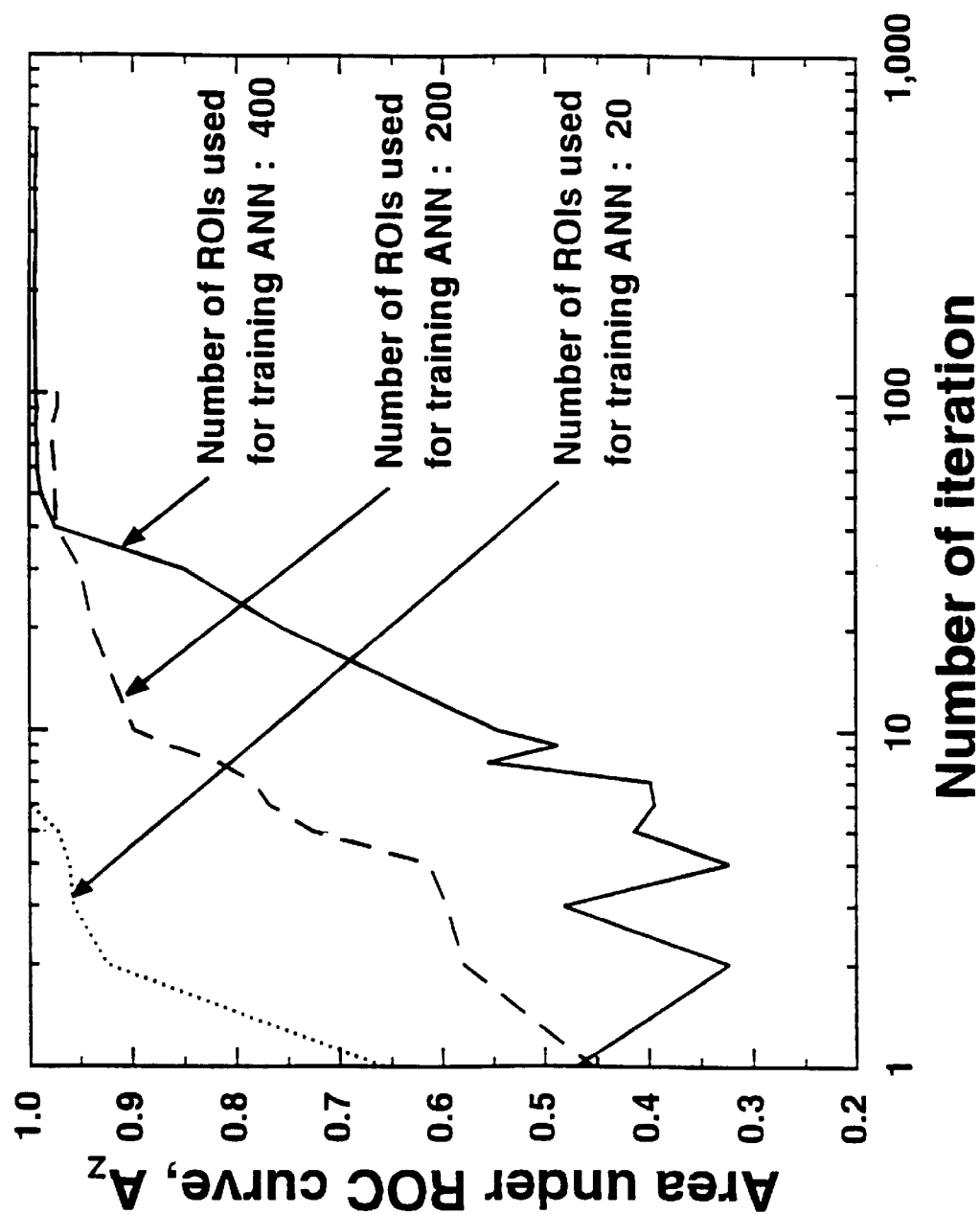

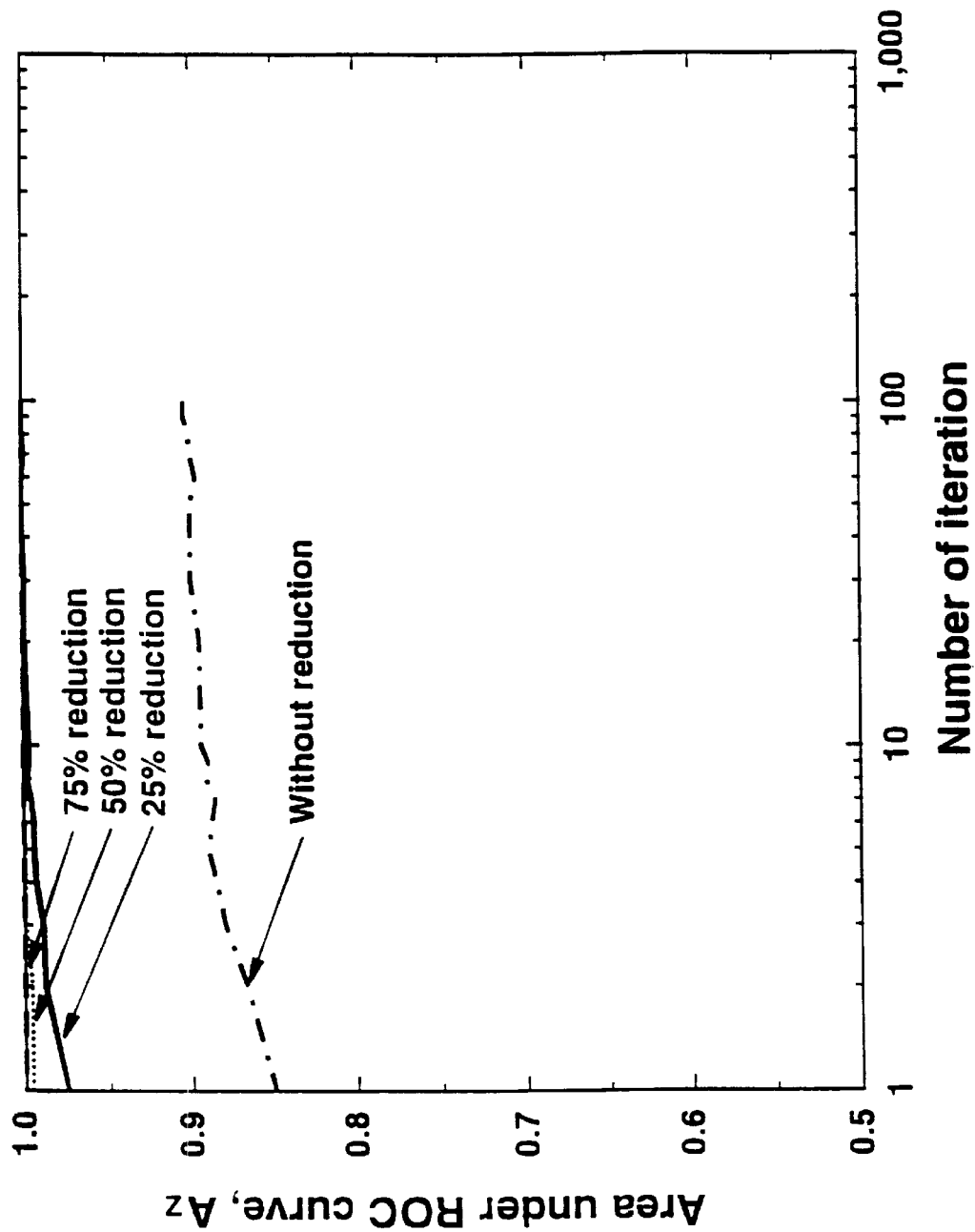

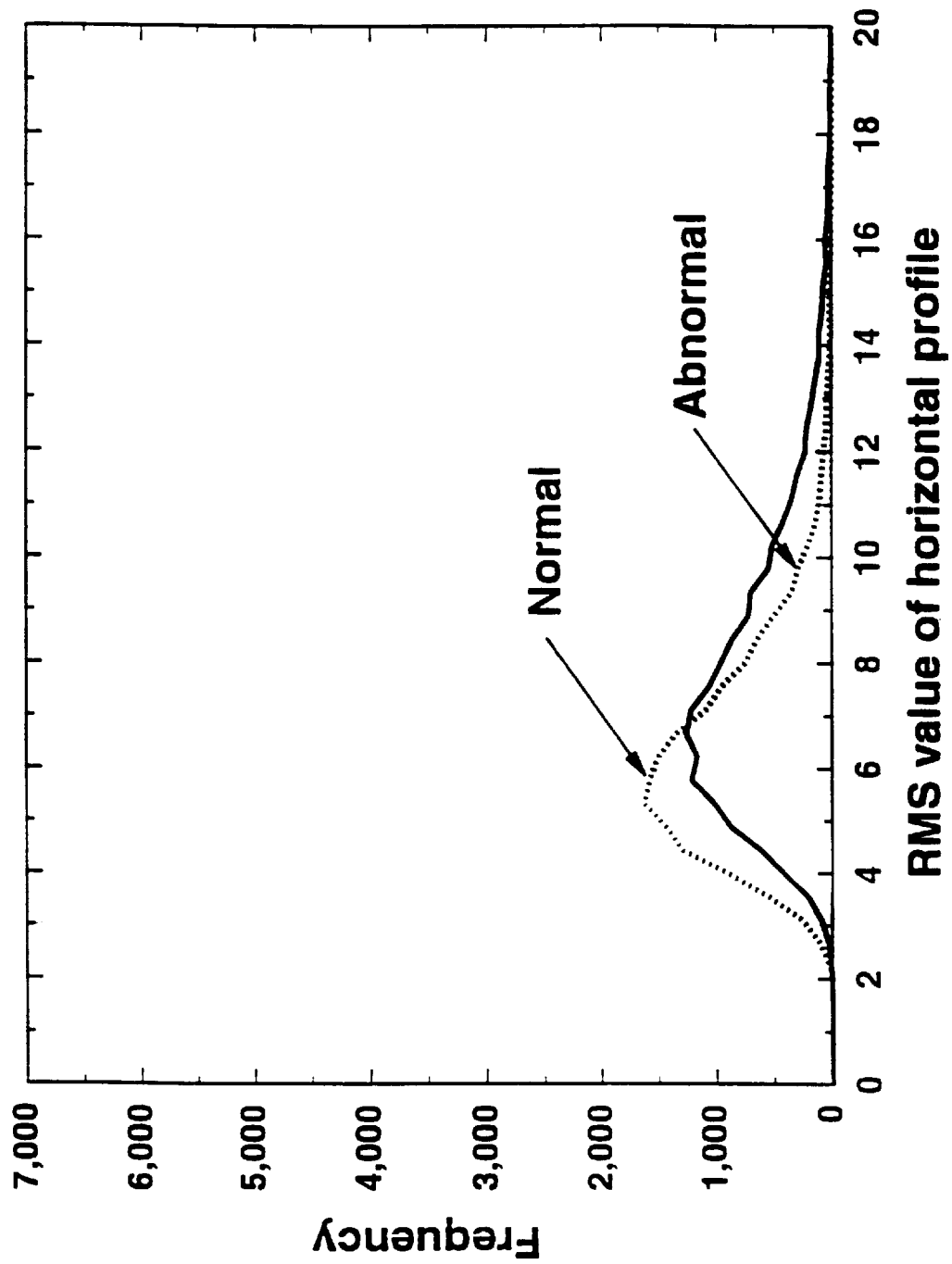

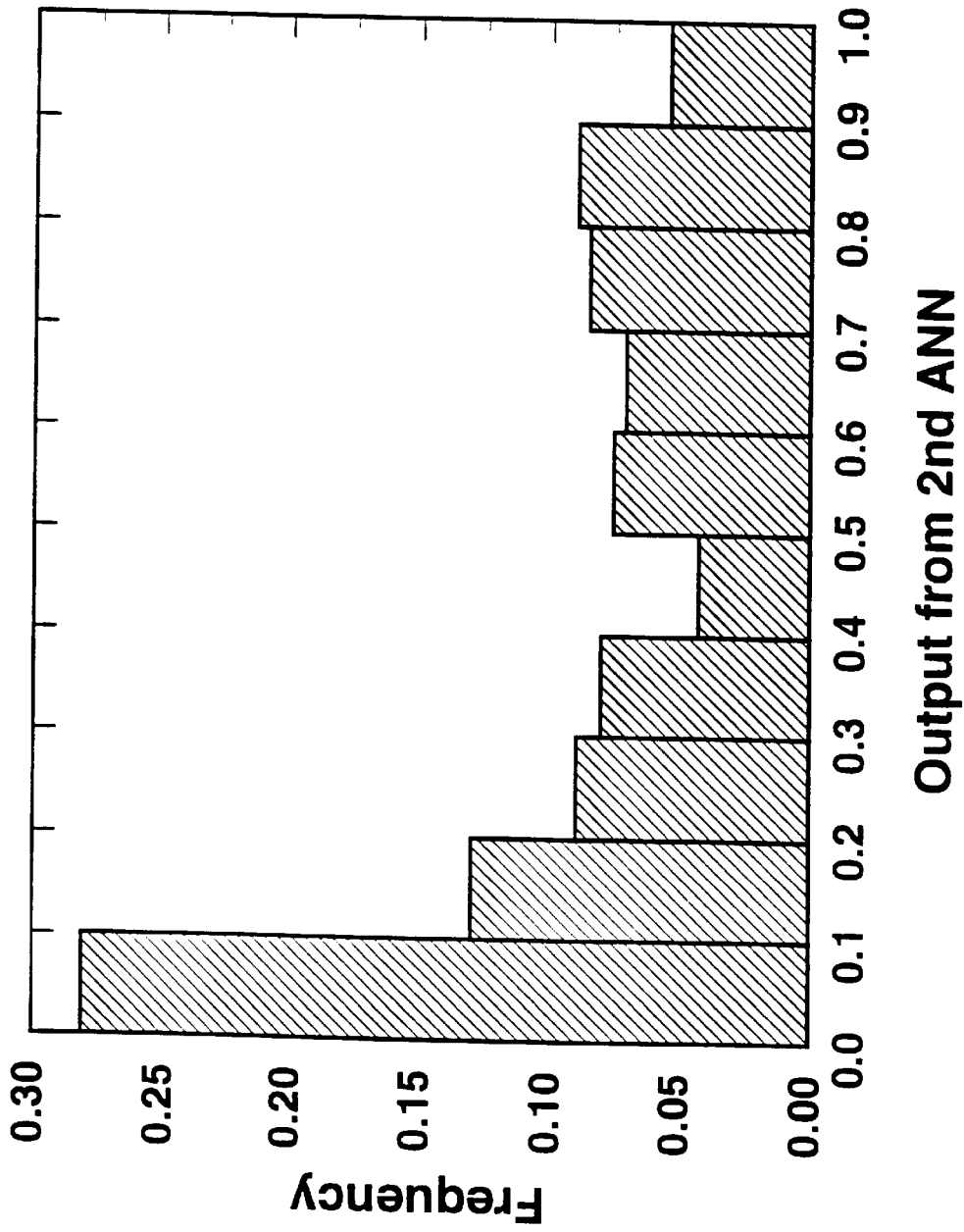
FIG. 15A Histogram of outputs from 2nd ANN for a normal case to be analyzed by 3rd ANN

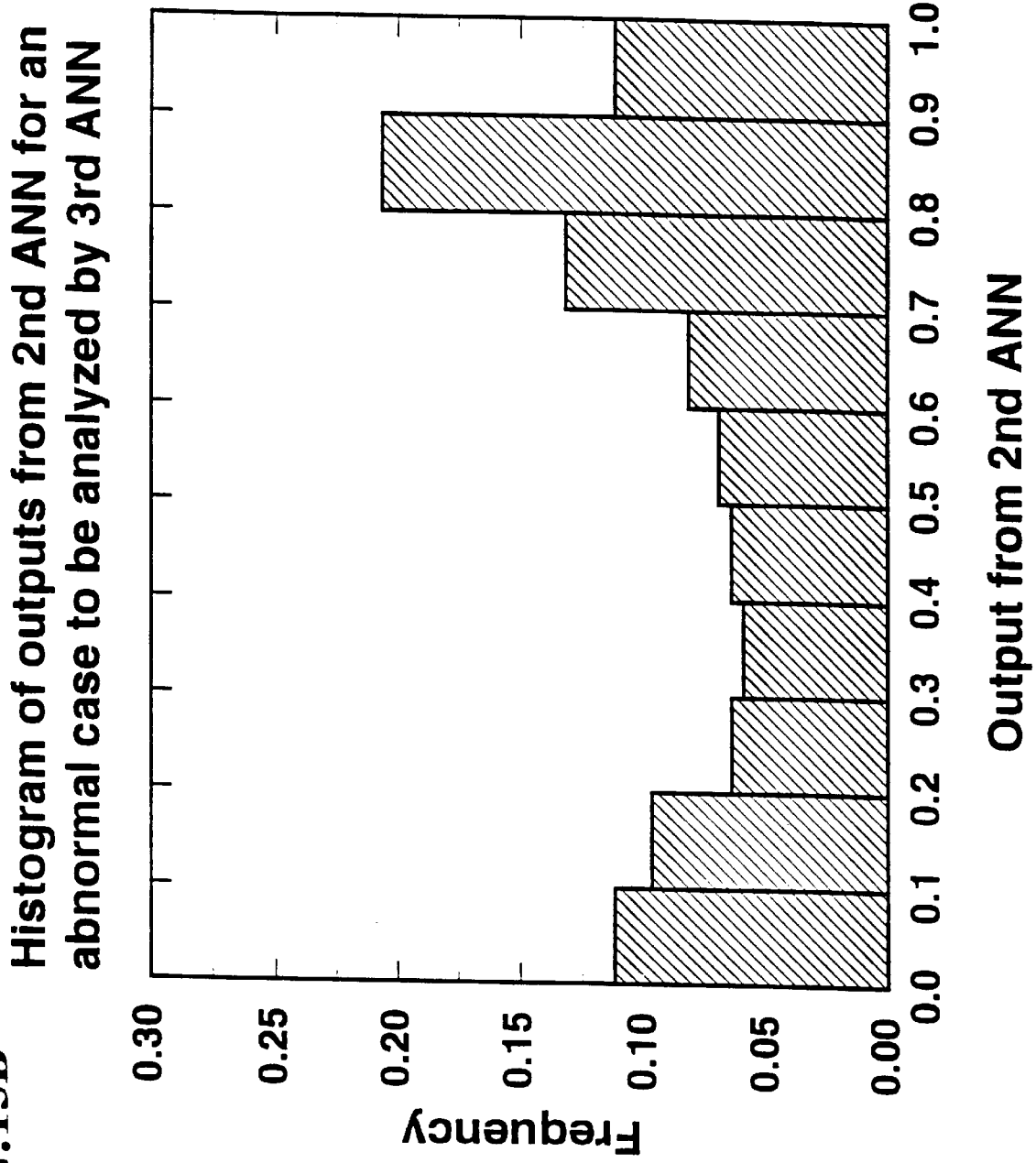
FIG.15B Histogram of outputs from 2nd ANN for an abnormal case to be analyzed by 3rd ANN Schematic diagram of the ANN analysis method applied to 3D array of pixel values (ROI) obtained from 3D image data

APPARATUS AND METHOD FOR COMPUTERIZED ANALYSIS OF INTERSTITIAL INFILTRATES IN CHEST IMAGES USING ARTIFICIAL NEURAL NETWORKS

GOVERNMENT SPONSORSHIP

This invention was made in part with U.S. Government support under grant numbers USPHS CA 62625, 60187 and 64370 from N.C.I., N.I.H. and D.H.H.S., and under grant number MRH 17-93-J-3021 and 71-96-1-6228 from the U.S. Army and the Department of Defense. The U.S. Government has certain rights in the invention.

BACKGROUND OF THE INVENTION

1. Field of the Invention

The present invention is directed to the analysis of radiographs using artificial neural networks which classify the radiographs into normal and abnormal.

2. Discussion of the Related Art

Interstitial lung disease is one of the most common findings in abnormal chest radiographs, as is described by H. MacMahon, K J M. Liu, S. M. Montner, and K. Doi, in "The nature and subtlety of abnormal findings in chest radiographs," Med. Phys. 18: 206–210 (1991). However, due to the subjectivity in the radiologists' interpretation of interstitial disease, the diagnosis of interstitial lung disease is considered a difficult task for radiologists because no quantitative criteria exists for distinction between normal patterns and subtle abnormal infiltrate patterns on chest radiographs. This subjectivity is reported in "Disagreement in chest Roentgen interpretation," Chest 68, 278–282 (1975) by P. G. Herman, D. E. Gerson, S. J. Hessel, B. S. Mayer, M. Watnick, B. Blesser and D. Ozonoff. Therefore, Applicants have been developing computer-aided diagnosis (CAD) schemes for quantitative analysis of interstitial infiltrates to improve diagnostic accuracy and reproducibility. Two different CAD schemes for detection and characterization of interstitial lung disease are disclosed in "Image feature analysis and computer-aided diagnosis in digital radiography: Detection and characterization of interstitial lung diseases in digital chest radiographs," Med. Phys. 15: 311–319 (1988) by S. Katsuragawa, K. Doi and H. MacMahon; "Image feature analysis and computer-aided diagnosis in digital radiography: Classification of normal and abnormal lungs with interstitial diseases in chest images," Med. Phys. 16: 38–44 (1989) by S. Katsuragawa, K. Doi and H. MacMahon; "Automated selection of regions of interest for quantitative analysis of lung textures in digital chest radiographs," Med. Phys. 20, 975–982 (1993) by X. Chen, K. Doi, S. Katsuragawa and H. MacMahon; "Computer-aided diagnosis for interstitial infiltrates in chest radiographs: Optical-density dependence of texture measures," Med. Phys. 22: 1515–1522 (1995) by J. Morishita, K. Doi, S. Katsuragawa, L. Monnier-Cholley and H. MacMahon; "Computerized analysis of interstitial infiltrates on chest radiographs: A new scheme based on geometric-pattern features and Fourier analysis," Acad. Radiol. 2, 455–462 (1995) by L. Monnier-Cholley, H. Macmahon, S. Katuragawa, J. Morishita and K. Doi; and "Quantitative analysis of geometric-pattern features of interstitial infiltrates in digital chest radiographs: Preliminary results," Journal of Digital Imaging 9, 137–144 (1996) by S. Katsuragawa, K. Doi, H. MacMahon, L. Monnier-Cholley, J. Morishita and T. Ishida, each of which is incorporated herein by reference. These schemes include texture analysis by use of Fourier transform and geometric-pattern analysis and extract image features associated with interstitial infiltrate patterns from digitized chest radiographs. These features are the RMS variation and the first moment of the power spectrum obtained by texture analysis which correspond to the magnitude and the coarseness (or fineness) of the infiltrates. In addition, by geometric-pattern analysis, the total area of the area components and the total length of the line components are obtained, which are related to the nodular opacity and linear opacity, respectively, in interstitial infiltrate patterns. Some useful information related to interstitial infiltrate patterns can be extracted by these schemes. Although the performance of these schemes is generally very good, there are still some cases in which normal and abnormal cases are not correctly determined. An example of the misclassification is reported in "Computer-aided diagnosis in chest radiography: Preliminary experience," Invest. Radio. 28, 987–993 (1993), by K. Abe, K. Doi, H. MacMahon, M. L. Giger, H. Hia, X. Chen, A. Kano, and T. Yanagisawa, incorporated herein by reference. Therefore, it is useful to develop an alternative approach based on image data in lung fields of chest radiographs.

Artificial neural networks (ANN) have been applied to several chest CAD schemes. "Potential usefulness of an artificial neural network for differential diagnosis of interstitial diseases: Pilot study," Radiology 177, 857–860 (1990) by N. Asada, K. Doi, H. MacMahon, S. M. Montner, M. L. Giger, C. Abe, and Y. Wu, examines differential diagnosis of interstitial lung diseases on the basis of clinical and radiographic information, whereas "Computerized analysis for automated detection of lung nodules in digitized chest radiographs," Ph.D. dissertation of the University of Chicago (1996), by X. W. Xu examines the elimination of false positives in the detection of lung nodules. ANNs used in these schemes were trained with some extracted features associated with lesions and/or false positives.

SUMMARY OF THE INVENTION

Accordingly, the present invention beneficially detects abnormal conditions by an improved automatic technique using ANNs trained with digital image data. Briefly, the preferred embodiment of the present invention is a method for operating a microprocessor which is ultimately embodied in code for controlling such microprocessor when such code is generated by a compiler. The inventive method uses samples taken from a medical image (e.g., chest x-ray, MRI, CAT scan, ultrasound) as inputs to a trained ANN to provide an analysis of whether a disease (e.g., interstitial lung disease) is shown in the medical image. The present invention advantageously uses a series of ANNs to provide a diagnosis. Each ANN converts from n-dimensional image data to (n−1) dimensional image data using one-dimensional ANNs, until a last one-dimensional ANN produces a partial diagnosis. Using this diagnosis in connection with a series of rules and a classification network, a complete diagnosis is generated.

According to the present invention, the number of connections required to make a complete diagnosis is greatly reduced in comparison to using fully connected two-dimensional neural networks. In addition, the training time required to train the complete network is reduced.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein:

FIG. 2D is a histogram showing the frequency of all input data for a unit of the $1^{st}$ ANN;

FIG. 7A is a graph showing the area under the ROC curve during a consistency test of the ANN trained with two-dimensional (32×32) chest image data for distinction between normal and abnormal ROIs;

FIG. 8A is a graph showing the effect of the reduction of training data to avoid contamination on a consistency test.

FIG. 10A is a histogram showing RMS values of each horizontal profile when using 32,000 profiles;

FIG. 15A is a histogram showing percentages of outputs from the $2^{nd}$ ANN for a normal case which is to be analyzed by a $3^{rd}$ ANN;

FIG. 15B is a histogram showing percentages of outputs from the $2^{nd}$ ANN for an abnormal case which is to be analyzed by a $3^{rd}$ ANN;

DESCRIPTION OF THE PREFERRED EMBODIMENT

For clarity, the examples below are described with reference to diagnosis of interstitial lung disease using two-dimensional regions of interest (ROIs) which are 32 pixels by 32 pixels. However, as would be evident to one of ordinary skill in the art in light of this disclosure, other diseases in other areas may also be diagnosed using the present technique. Further, since the size of abnormalities varies with a type of disease, the size of the ROIs also may vary to match the size of the abnormalities, including using rectangular, circular or oval ROIs. Also, the present invention encompasses the use of plural neural networks to analyze three- and four-dimensional image data of any configuration.

In one study, a database, including 100 normal and 100 abnormal postero-anterior (PA) chest radiographs which were taken with Lanex Medium screens and OC film (Eastman Kodak, Rochester, N.Y.) were used, although other screens and films would be amenable for use with the disclosed method. The normal cases were chosen by four experienced chest radiologists on the basis of unequivocally normal radiographs in terms of clinical data and follow-up chest radiographs. The abnormal cases of interstitial lung disease with varying severity were selected based on radiologic findings, CT, clinical data, and/or follow-up radiographs, by consensus of the same radiologists. The abnormal cases contained interstitial infiltrates in more than 20% of the area of both lung fields. Twenty-six cases had focal interstitial infiltrates encompassing 20–50% of the lung area. The other abnormal cases had diffuse interstitial infiltrates involving more than 50% of the lung area. These abnormal cases were previously cited by L. Monnier-Cholley, H. MacMahon, S. L. Katsuragawa, J. Morishita and K. Doi, in "Computerized analysis of interstitial infiltrates on chest radiographs: A new scheme based on geometric pattern features and Fourier analysis," Acad. Radiol. 2, 455–462 (1995), incorporated herein by reference. Chest radiographs were digitized by using a laser scanner (KFDR-P Konica Corp., Tokyo, Japan) with a 0.175 mm pixel size and 1024 gray levels and an IBM RISC/6000 Power station (Model 590) was used for development of our CAD scheme. Here also, other devices, i.e., scanners and computers; can replace the specific scanner and computer described herein.

Figure 1A:
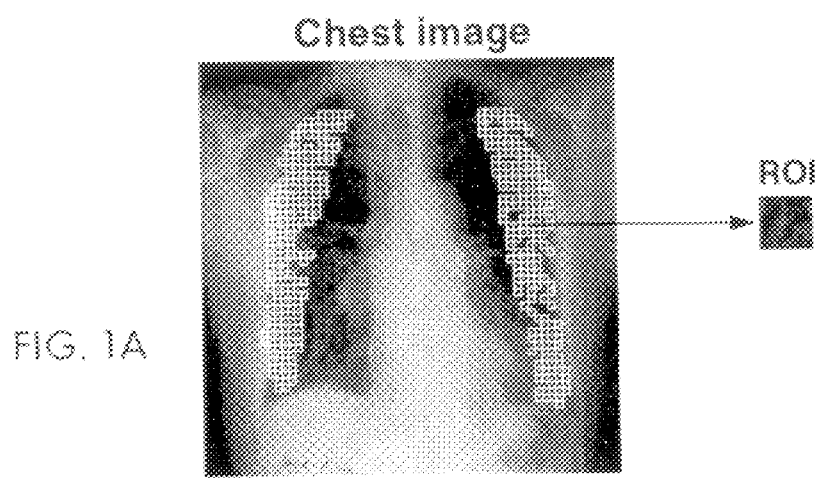
FIG. 1A is a screen capture of a chest image and an exploded view of a region of interest (ROI) of the chest image.
Figure 1B:
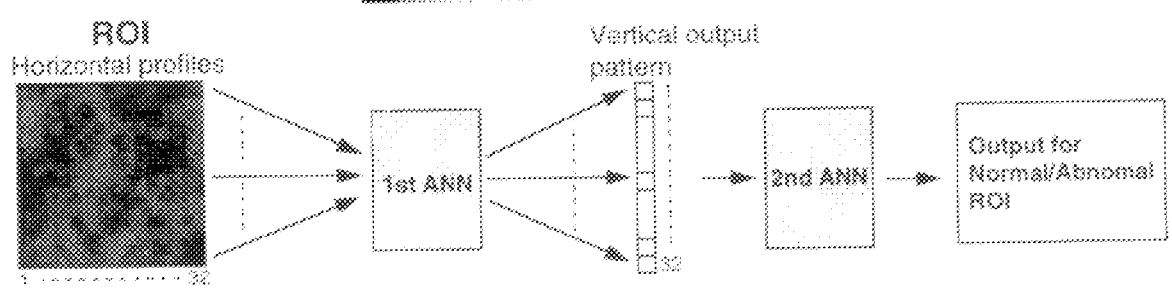
FIG. 1B is a schematic diagram showing a series of ANNS for analyzing interstitial infiltrates in chest images.

The screen capture of FIG. 1A shows a chest image broken into several hundreds of square regions of interest (ROIs) which can be applied to ANNs configured and trained according to the present invention. The block diagram of the ANN analysis system is shown in FIG. 1B. When using the trained system to aid in diagnosis, first, the ROIs are automatically selected from medical images (e.g., normal and abnormal chest radiographs). The method for automated selection of ROIs is described in detail in "Automated selection of regions of interest for quantitative analysis of lung textures in digital chest radiographs," Med. Phys. 20, 975–982 (1993) by X. Chen, K. Doi, S. Katsuragawa and H. MacMahon, incorporated herein by reference. The matrix size of the illustrated ROI is 32×32 (5.6×5.6 mm$^2$). The two-dimensional distribution of pixel values in an ROI is considered to consist of 32 one-dimensional horizontal profiles, each of which includes 32 pixel values along the horizontal direction. We employed two different ANNs for detecting interstitial infiltrates. The one-dimensional horizontal profiles in each ROI were subjected to a trend correction based on a surface fitting technique and then entered into the $1^{st}$ ANN for distinction between normal and abnormal profiles. (This trend correction is described in "Image feature analysis and computer-aided diagnosis in digital radiography: Detection and characterization of interstitial lung diseases in digital chest radiographs," Med. Phys. 15: 311–319 (1988), by S. Katsuragawa, K. Doi, H. MacMahon, incorporated herein by reference). The output value for each one-dimensional horizontal profile is obtained from a corresponding part of the $1^{st}$ ANN and ranges from 0 to 1, which represents the degree of normality/abnormality (0: normal; 1: abnormal), for each horizontal profile. Since each ROI has 32 horizontal profiles, 32 outputs corresponding to the 32 profiles for each ROI are obtained from the $1^{st}$ ANN. These 32 outputs are combined into a sequence of outputs called a vertical output pattern. The vertical output pattern is entered into the $2^{nd}$ ANN, and the output value of the $2^{nd}$ ANN is used for distinguishing between normal and abnormal ROIs. The output value which represents the degree of normality/abnormality (0: normal, 1: abnormal), for each ROI. Finally, a rule-based classification method is employed for distinguishing between normal and abnormal cases with interstitial infiltrates.

Figure 1C:
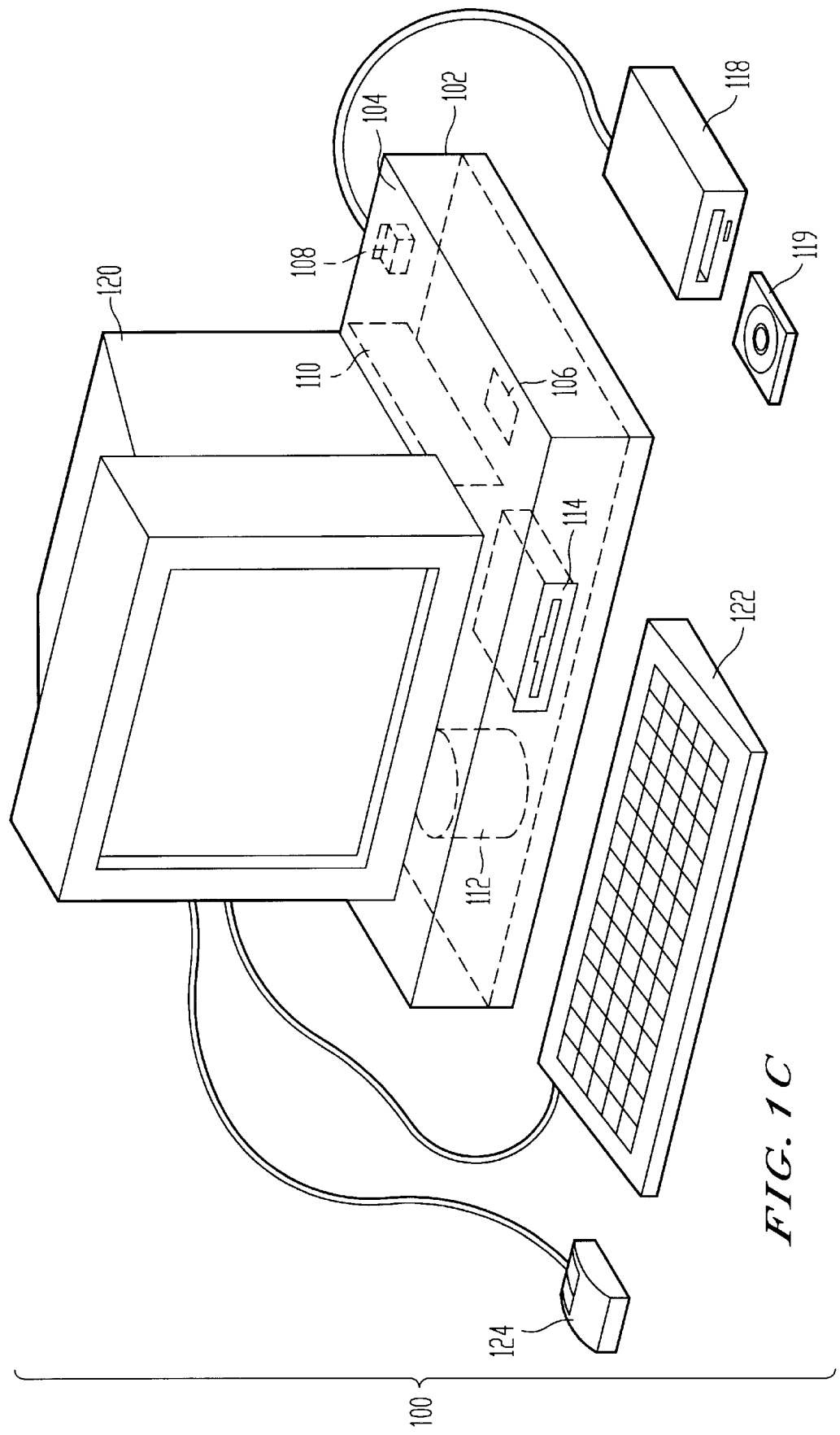
FIG. 1C is a schematic illustration of a computer system for implementing the method of the present invention.

As shown in FIG. 1C, a computer 100 implements the method of the present invention, wherein the computer housing 102 houses a motherboard 104 which contains a CPU 106, memory 108 (e.g., DRAM, ROM, EPROM, EEPROM, SRAM and Flash RAM), and other optional special purpose logic devices (e.g., ASICs) or configurable logic devices (e.g., GAL and reprogrammable FPGA). The computer 100 also includes plural input devices, (e.g., a keyboard 122 and mouse 124), and a display card 110 for controlling monitor 120. In addition, the computer system 100 further includes a floppy disk drive 114; other removable media devices (e.g., compact disc 119, tape, and removable magneto-optical media (not shown)); and a hard disk 112, or other fixed, high density media drives, connected using an appropriate device bus (e.g., a SCSI bus or an Enhanced IDE bus). Although compact disc 119 is shown in a CD caddy, the compact disc 119 can be inserted directly into CD-ROM drives which do not require caddies. Also connected to the same device bus or another device bus as the high density media drives, the computer 100 may additionally include a compact disc reader 118, a compact disc reader/writer unit (not shown) or a compact disc jukebox (not shown). In addition, a printer (not shown) also provides printed listings of diagnoses.

The system further includes at least one computer readable media. Examples of such computer readable media are compact discs 119, hard disks 112, floppy disks, tape, magneto-optical disks, PROMs (EPROM, EEPROM, Flash EPROM), DRAM, SRAM, etc. Stored on any one or on a combination of the computer readable media, the present invention includes software for controlling both the hardware of the computer 100 and for enabling the computer 100 to interact with a human user. Such software may include, but is not limited to, device drivers, operating systems and user applications, such as development tools. Such computer readable media further includes the computer program product of the present invention for analyzing medical images in assessing the presence of a diseased condition.

A three-layer feed-forward neural network is employed for the $1^{st}$ ANN. The ANN has 32 input units, 16 hidden units, and 1 output unit. For training of the $1^{st}$ ANN, we initially selected "representative" ROIs for normal and abnormal cases based on single texture indices obtained by texture analysis. The texture analysis technique is described in "Image feature analysis and computer-aided diagnosis in digital radiography: Classification of normal and abnormal lungs with interstitial diseases in chest images," Med. Phys. 16: 38–44 (1989) by S. Katsuragawa, K. Doi, H. MacMahon, incorporated herein by reference. The normal ROIs for this study were randomly selected from ROIs in normal chest images in a database where texture indices of ROIs are in the mid-30% range (from 35% to 65%) of all data in each case. The abnormal ROIs are also randomly selected from ROIs in abnormal chest images, in which the texture indices of ROIs are in the upper 30% range (from 5% to 35%) of all data in each case. Although "representative" ROIs were selected by using a texture index, it should be noted that some "normal" ROIs still include horizontal profiles that may appear "abnormal" mainly due to rib edges and/or sharp edge vessels. In addition, "abnormal" ROIs may include some horizontal profiles with very weak interstitial infiltrates and thus may appear "normal".

Therefore, we attempted to reduce such "contaminated" training data by use of the RMS value of each profile. For the final selection of training data for normals, horizontal profiles with large RMS values in the upper 25% of normal cases were eliminated. For the training data of abnormals, we eliminate horizontal profiles with small RMS values in the lower 25% of abnormal cases.

Figure 2A:
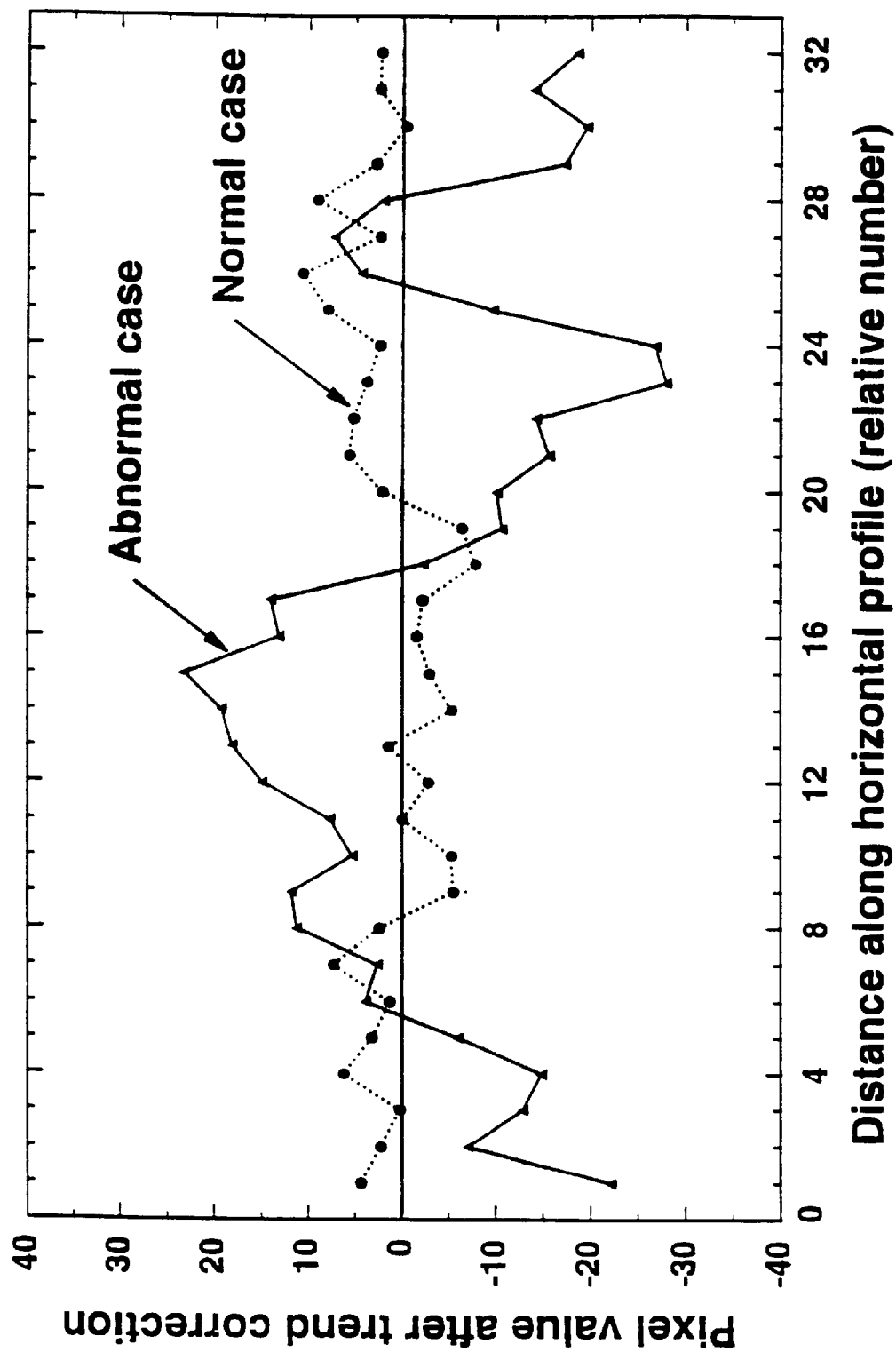
FIG. 2A is a graph showing horizontal profiles obtained from normal and abnormal chest images.
Figure 2B:
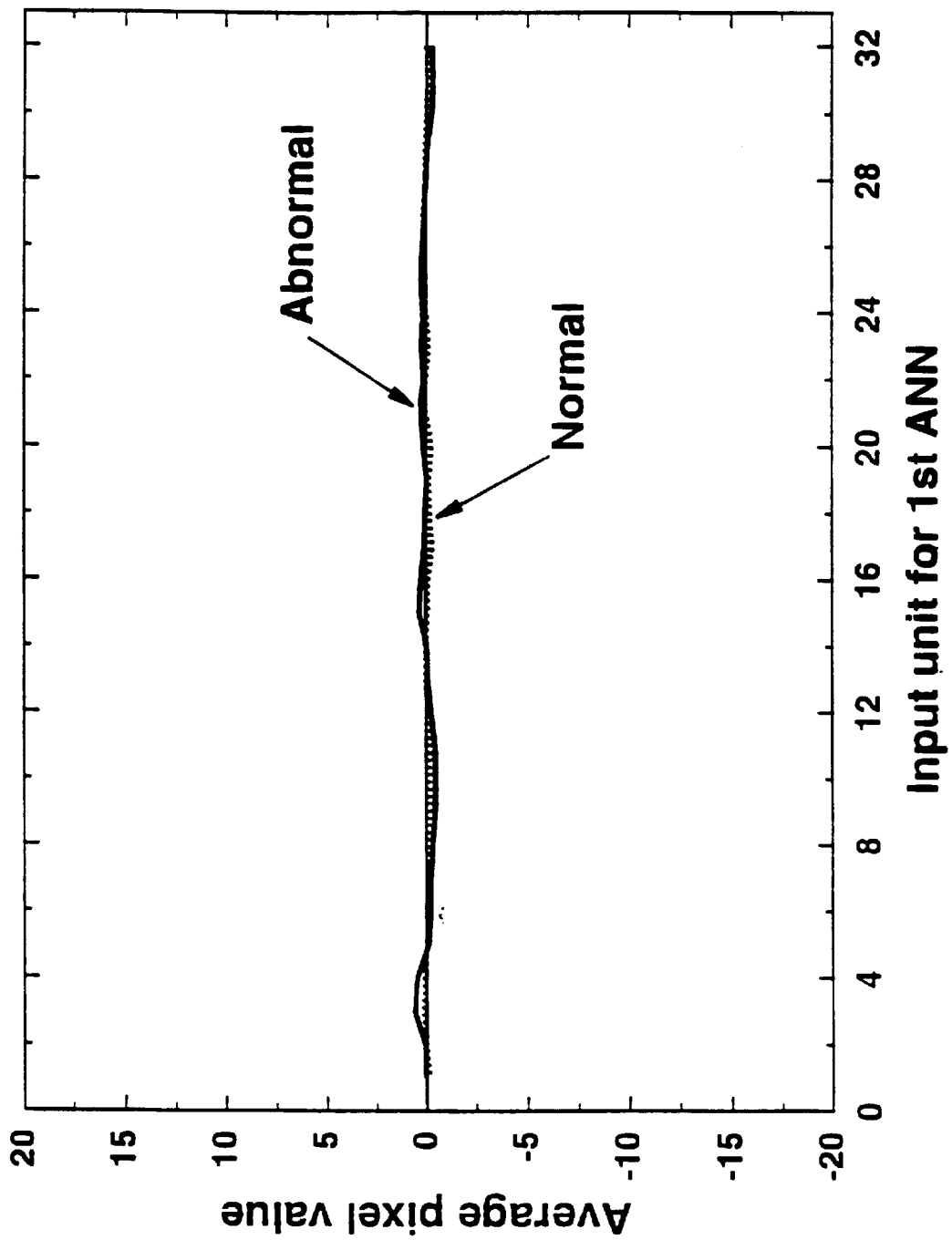
FIG. 2B is a graph showing average pixel value of all input data at each input.
Figure 2C:
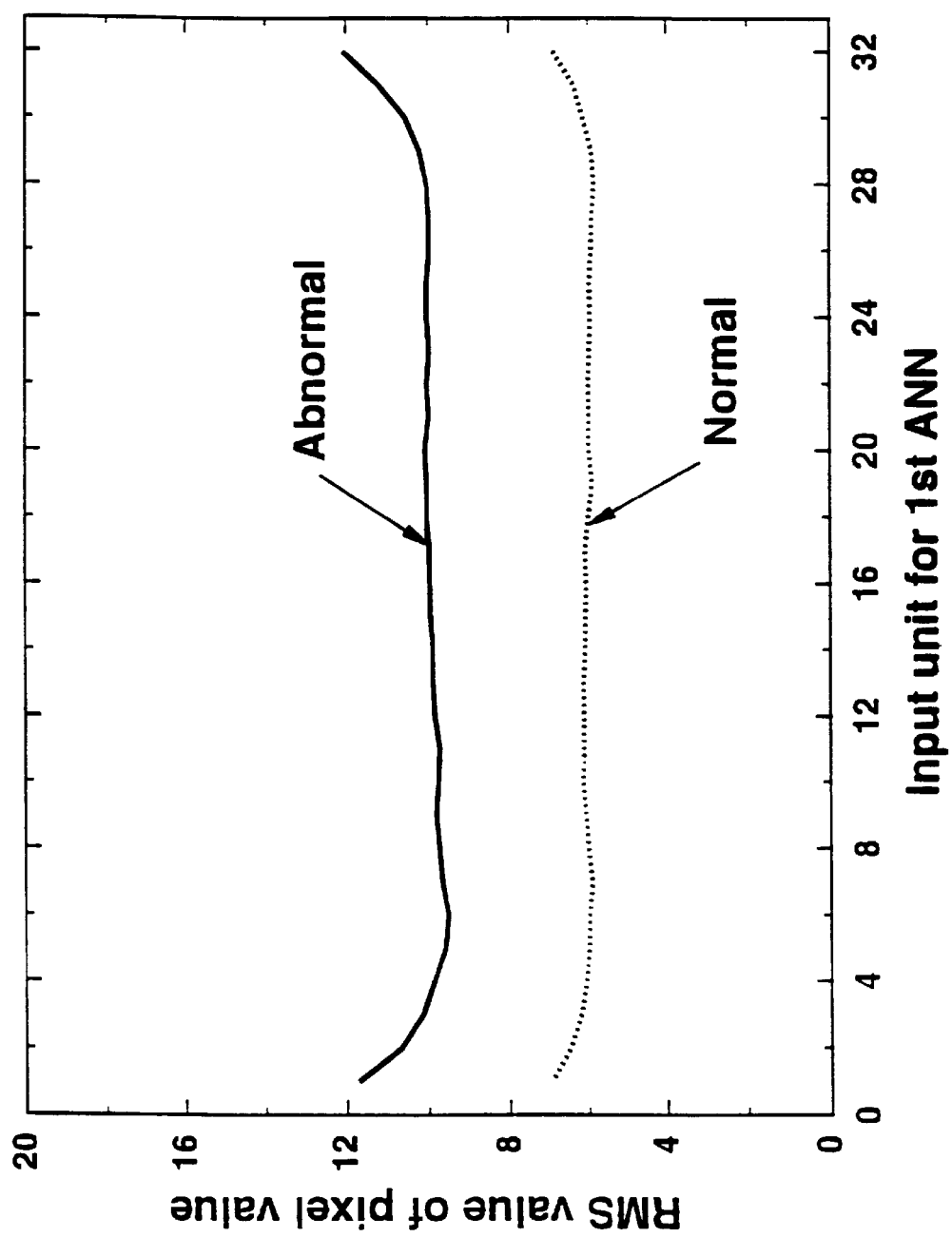
FIG. 2C is a graph showing RMS value of all input data at input unit.

The horizontal profiles of a normal case and an abnormal case are shown in FIG. 2A. It is apparent in FIG. 2A that the variation of pixel values in the abnormal profile is larger than that in the normal case. The average pixel values and the RMS values of all input data at each input unit for the $1^{st}$ ANN are shown in FIGS. 2B and 2C, respectively. Since the trend correction technique is applied to all of the ROIs, the average values are very close to zero at all input units. It is evident that RMS values of abnormal cases are greater than those of normals at all input units because the variation of the horizontal profiles with interstitial infiltrates is usually larger than that of normals. The RMS values at the left and the right three units increased slightly, as shown in FIG. 2C, because the fitting error for trend correction tends to be large near the edges of ROIs. FIG. 2D is a histogram showing input data (normals and abnormals) used for a unit of the $1^{st}$ ANN. The distribution for abnormal cases was broader than that for normal cases. The two distributions are very similar to Gaussian distributions.

The $2^{nd}$ ANN has the same structure as that of the $1^{st}$ ANN, i.e., a three-layer feed-forward neural network with 32 input units, 16 hidden units and 1 output unit. The $2^{nd}$ ANN is trained with vertical output patterns which correspond to the outputs from the $1^{st}$ ANN for all of the horizontal profiles included in each ROI. When training the $2^{nd}$ ANN, "representative" ROIs for normals and abnormals are selected initially in the same way as those used for training of the 1$^{st}$ ANN. However, the ROIs selected for training of the 2$^{nd}$ ANN did not overlap with the ROIs used for training of the 1$^{st}$ ANN. In order to reduce the effect of "contamination" in the training data, the average value of vertical output patterns was determined. For training data of normal ROIs, ROIs with large average values (upper 10% of normal ROIs) of vertical output patterns were eliminated. For training data of abnormal ROIs, ROIs with small average values (lower 10% of abnormal ROIs) were eliminated. After training, the output of the 2$^{nd}$ ANN is used to distinguish between normal and abnormal ROIs with interstitial infiltrates.

Figure 3A:
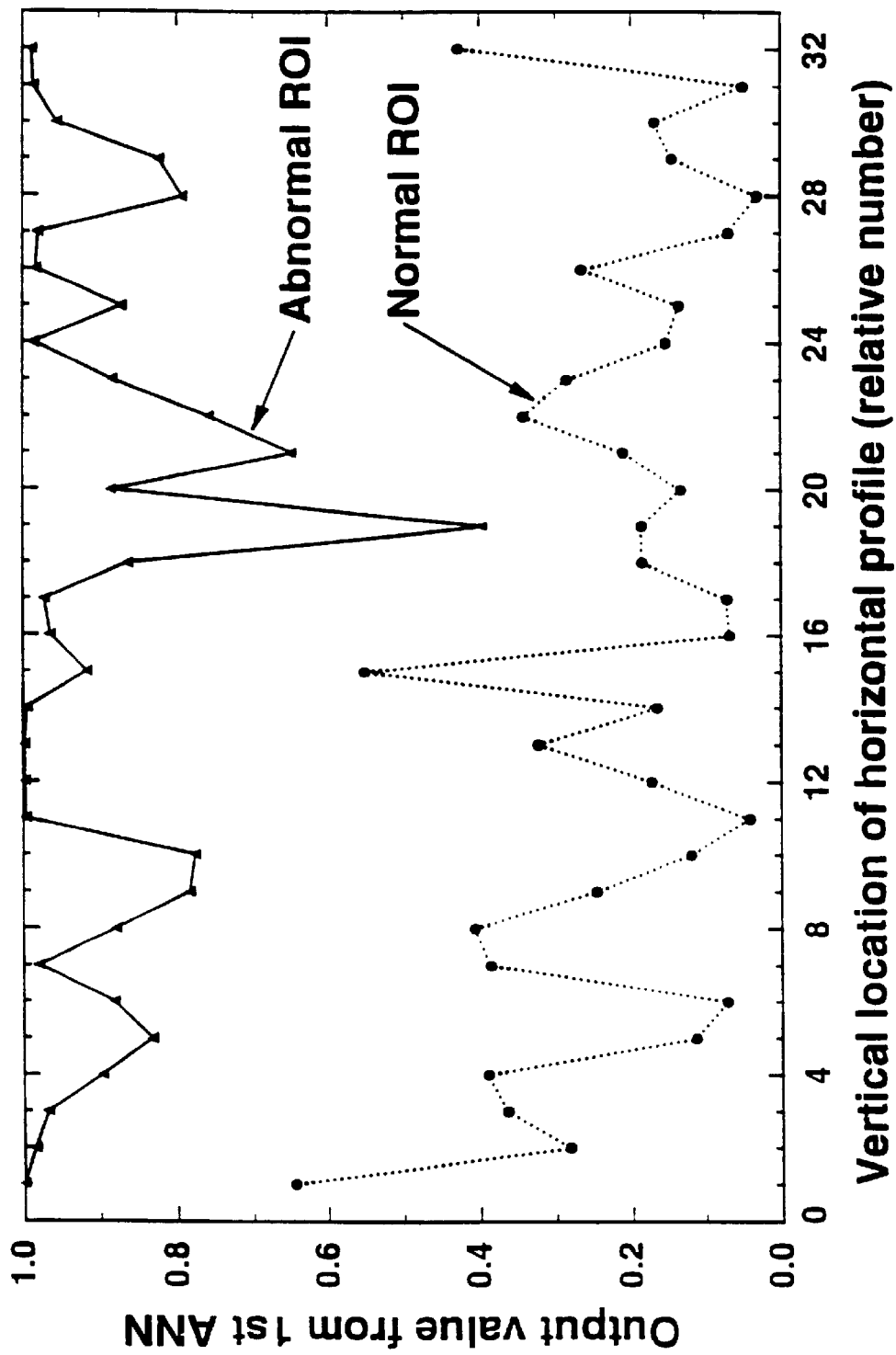
FIG. 3A is a graph showing vertical output patterns obtained from normal and abnormal ROIs.
Figure 3B:
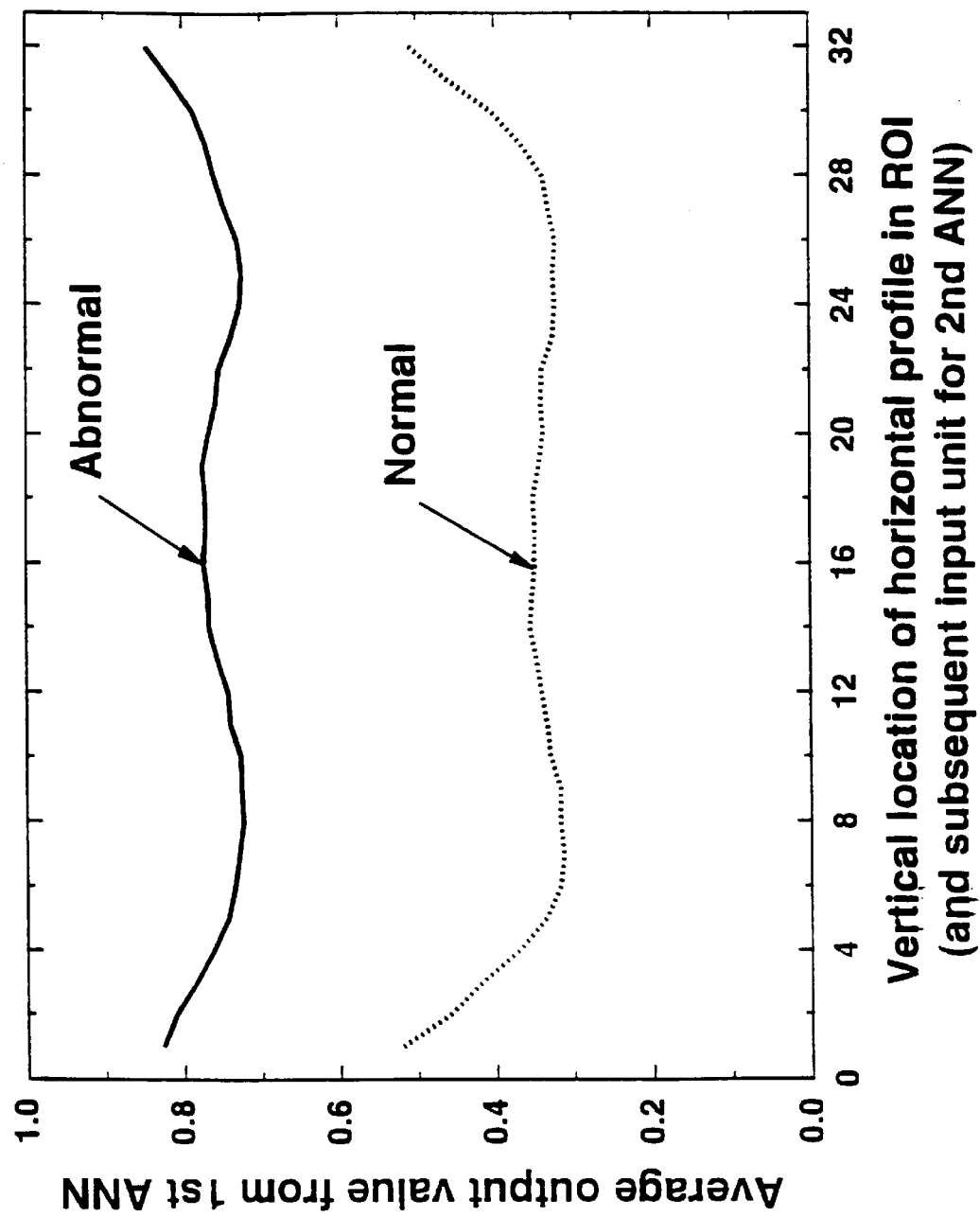
FIG. 3B is a graph showing average output value from the $1^{st}$ ANN and subsequent input data for each input unit of the $2^{nd}$ ANN.
Figure 3C:
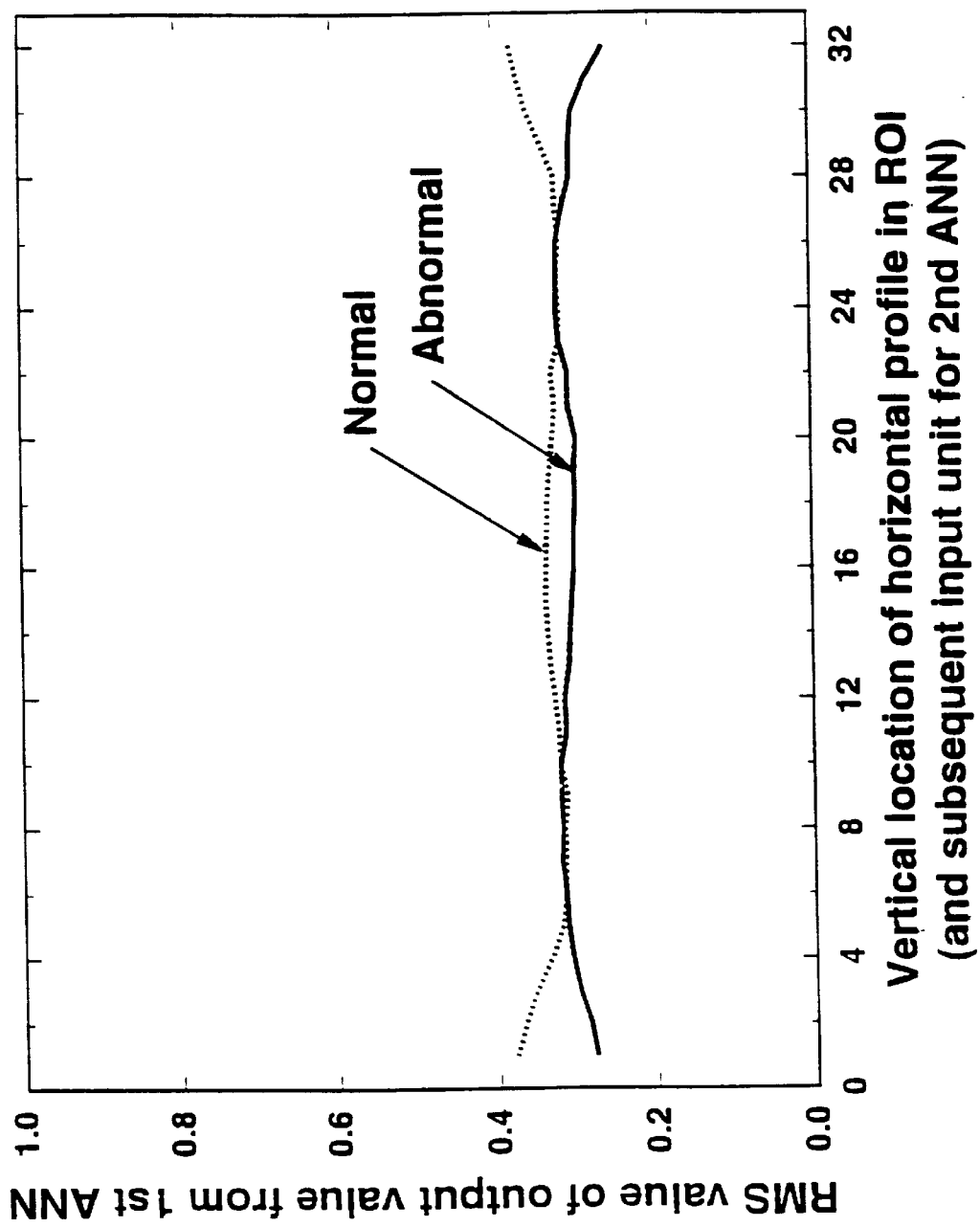
FIG. 3C is a graph showing RMS values of output values from the $1^{st}$ ANN for each vertical location of horizontal profiles in ROI.

Vertical output patterns (i.e., the outputs of the 1$^{st}$ ANN for each of the 32 horizontal profiles) for a normal and an abnormal ROI are shown in FIG. 3A. It is evident that the output value from the 1$^{st}$ ANN of an abnormal ROI is usually larger than that of a normal ROI. The average values and the RMS values of all input data at each input unit for the 2$^{nd}$ ANN are shown in FIGS. 3B and 3C, respectively. Since the outputs from the 1$^{st}$ ANN for the abnormal ROI tend to be large, the average output value for abnormal cases is greater than that for normal cases at all input units. However, the RMS value of the output from the 1$^{st}$ ANN for abnormal ROIs is very similar to that for normal ROIs.

The overall classification for a chest image between normal and abnormal cases is performed by a rule-based method. If the output of the 2$^{nd}$ ANN is greater than a predetermined threshold value, the ROI is considered abnormal. If the ratio of the number of abnormal ROIs to the total number of all ROIs in a chest image is greater than a certain threshold value, then the chest image is classified as abnormal. In addition, in an alternative embodiment, a 3$^{rd}$ ANN was applied to distinguish between normal and abnormal chest images, as is discussed in greater detail below.

Figure 4:
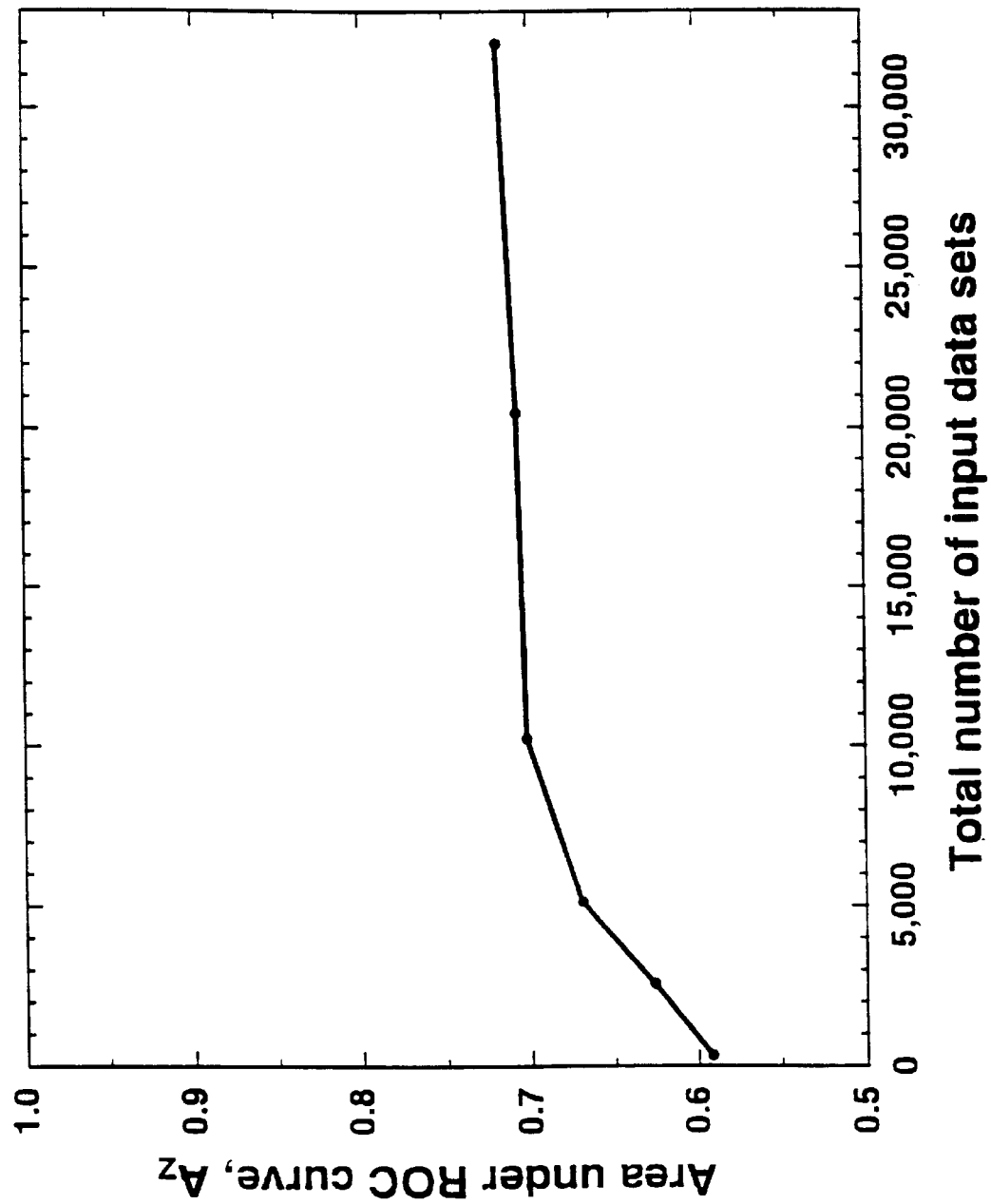
FIG. 4 is a graph showing the effect of the total number of input data sets used for training of the $1^{st}$ ANN.

In order to investigate the effect of the total number of input data sets used for training of the 1$^{st}$ ANN, ROIs were randomly selected from 10 normal cases and from 10 abnormal cases with severe interstitial infiltrates. A range of 320 to 32,000 horizontal profiles (10 to 1,000 ROIs) were used and their results were compared. One half of the input data were selected from normal cases and the other half from abnormal cases. For the validation test of the 1$^{st}$ ANN, however, a total of 12,800 horizontal profiles (200 normal and 200 abnormal ROIs) were randomly selected from 20 normal and 20 abnormal cases with various severities of interstitial infiltrates which were not used as training cases. The effect of the total number of training data for the 1$^{st}$ ANN is shown in FIG. 4. The $A_z$ values (areas under the ROC curve) increased gradually as the number of input data sets to the 1$^{st}$ ANN increased from 320 to 10,240. The classification performance with more than 10,240 input data sets increased only very slightly. The result indicates that the number of training data sets for the 1$^{st}$ ANN should be more than 10,000 horizontal profiles.

To evaluate the classification performance, the database of 100 normal and 100 abnormal cases with interstitial infiltrates was randomly divided into two groups. One was a data set for training, and another for testing. Each data set included 50 normal and 50 abnormal cases. Four different pairs of data sets were prepared for the evaluation of overall performance. The average $A_z$ value in distinguishing between normal and abnormal cases was 0.906±0.021 by use of the ANN scheme. This high classification rate indicates that the ANN scheme is useful for detection of interstitial infiltrates in digital chest images.

Figure 5:
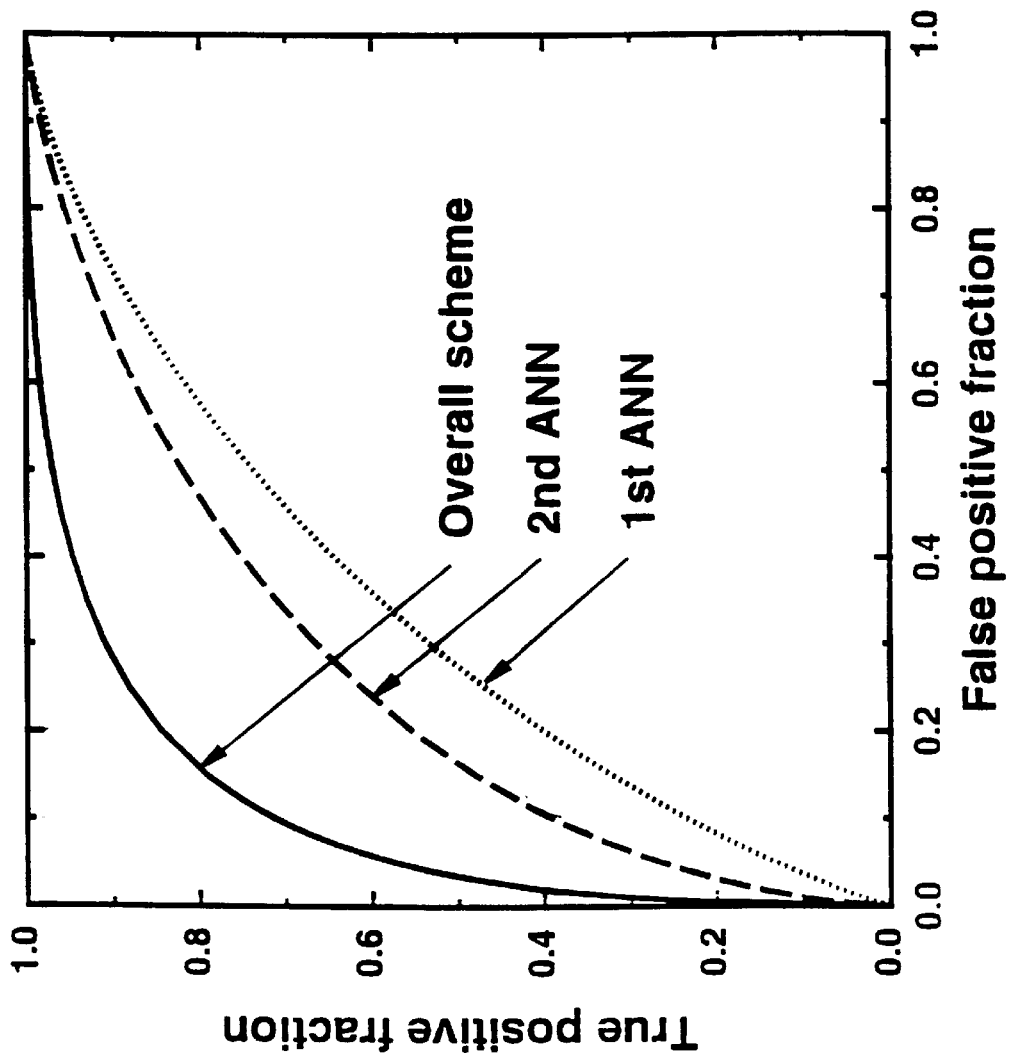
FIG. 5 shows ROC curves for the $1^{st}$ ANN, the $2^{nd}$ ANN and the overall scheme in distinguishing between normals and abnormals.
Figure 6A:
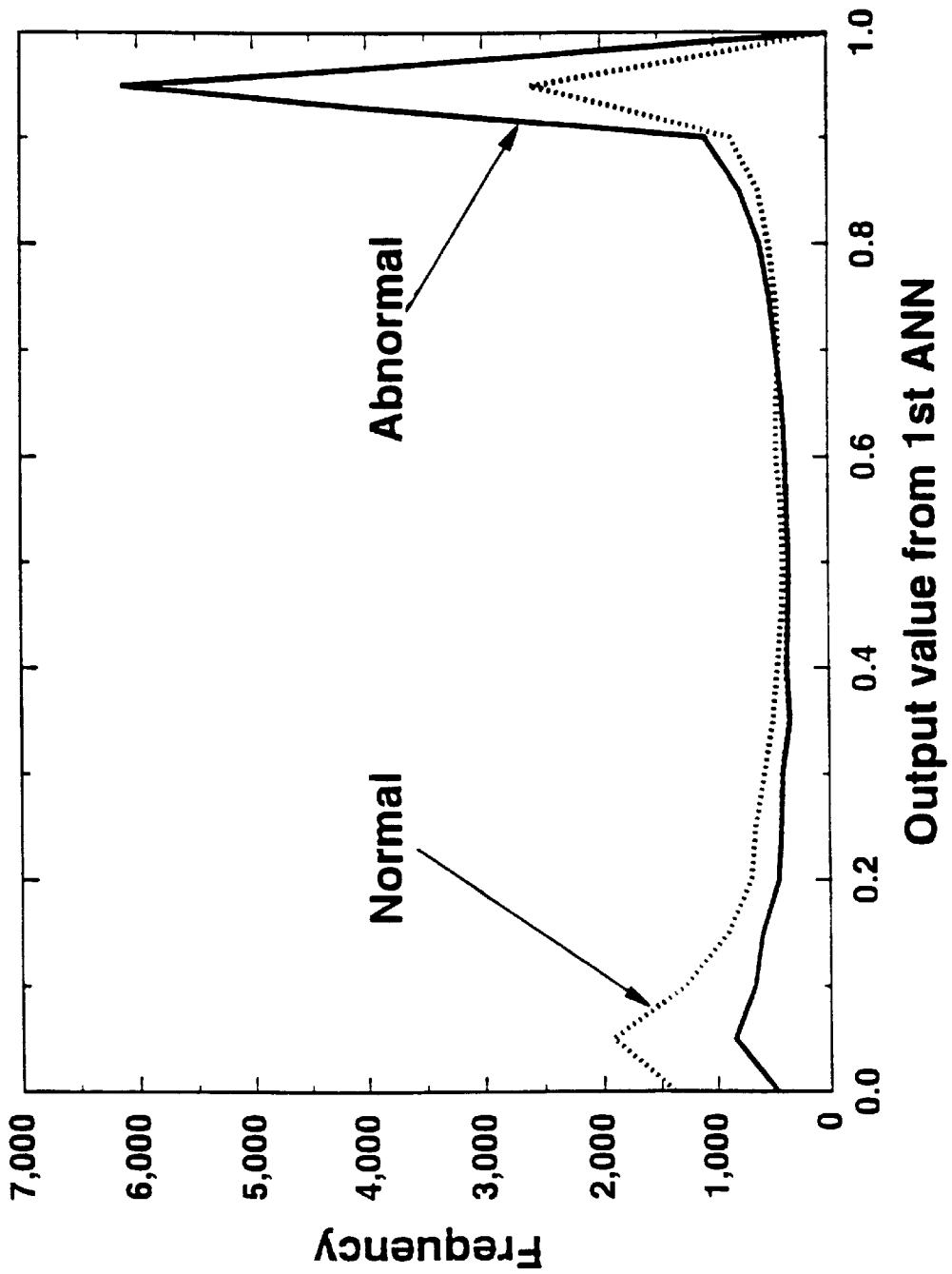
FIG. 6A is a histogram showing output values from the $1^{st}$ ANN in a validation test using 32,000 profiles.

One of the overall classification performances and the individual performance of the 1$^{st}$ and of the 2$^{nd}$ ANN, which were obtained by ROC analysis with the continuous rating scale (LABROC4 program), are shown in FIG. 5. The LABROC4 program is described in "ROC methodology in radiographic imaging," Invest. Radiol. 21, 720–733 (1986) by C. E. Metz; "Some practical issues of experimental design and data analysis in radiographical ROC studies," Invest. Radiol. 24 234–245 (1989) by C. E. Metz; and "New methods for estimating a binormal ROC curve from continuously-distributed test results," Invited for presentation at the 1990 Joint Statistical Meeting of the American Statistical Society and the Biometric Society, Anaheim, Calif.: 1990, by C. E. Metz, J-H Shen, and B. A. Herman, each of which is incorporated herein by reference. The ROC curve of the overall scheme was high ($A_z$=0.905). However, the classification performance on normal and abnormal profiles by the 1$^{st}$ ANN ($A_z$=0.669) was not high. This poor performance was probably due to the fact that some normal ROIs include "abnormal-like" profiles caused by rib edges and/or sharp edge vessels; also, some abnormal ROIs include "normal-like" profiles caused by extremely weak interstitial infiltrates. FIG. 6A is a histogram showing frequencies of output values which were obtained from the 1$^{st}$ ANN for normal and abnormal horizontal profiles. The histogram for normals contains two peaks, one at each end.

The output values for "clearly" normal patterns would contribute to a peak at low output values, whereas another peak at high output values would be due to horizontal profiles with rib edges and/or sharp edge vessels. The histogram for abnormals also indicates two peaks. The output values for "clearly" abnormal patterns would cause a sharp peak at high output values, whereas the other small peak at low output values may be derived from horizontal profiles which probably do not contain clear patterns due to interstitial infiltrates.

Figure 6B:
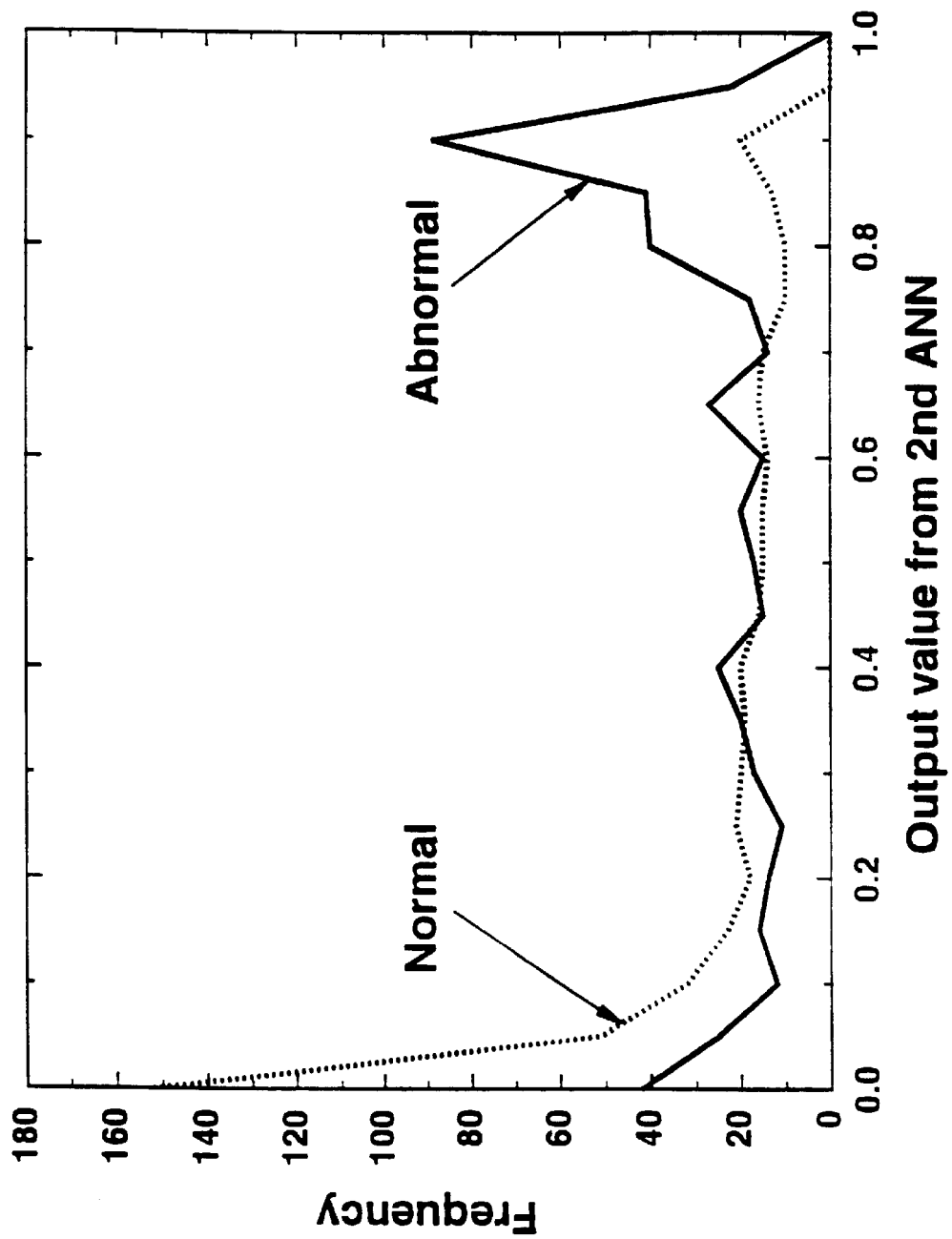
FIG. 6B is a histogram showing output values from the $2^{nd}$ ANN in a validation test using 1,000 ROIs.

FIG. 6B shows the histograms of all output values that were obtained from the 2$^{nd}$ ANN for normal and abnormal ROIs. These histograms from the 2$^{nd}$ ANN are similar to the histograms of the output from the 1$^{st}$ ANN. The output values of normal ROIs tend to converge at low levels. The performance of the 2$^{nd}$ ANN ($A_z$=0.750) was greater than that of the 1$^{st}$ ANN. If the majority of horizontal profiles in a normal ROI are "normal" patterns, the 2$^{nd}$ ANN can recognize the ROI as normal, even if the ROI includes a few contaminated horizontal profiles, i.e., a few outputs from the 1$^{st}$ ANN can have large values, as shown in FIG. 3A. In a similar way, when the majority of the horizontal profiles in an abnormal ROI contain interstitial infiltrate patterns, the second ANN can recognize the ROI as abnormal, even if the ROI has a few contaminated horizontal files. Therefore, the performance of the 2$^{nd}$ ANN was better than that of the 1$^{st}$ ANN.

Figure 7B:
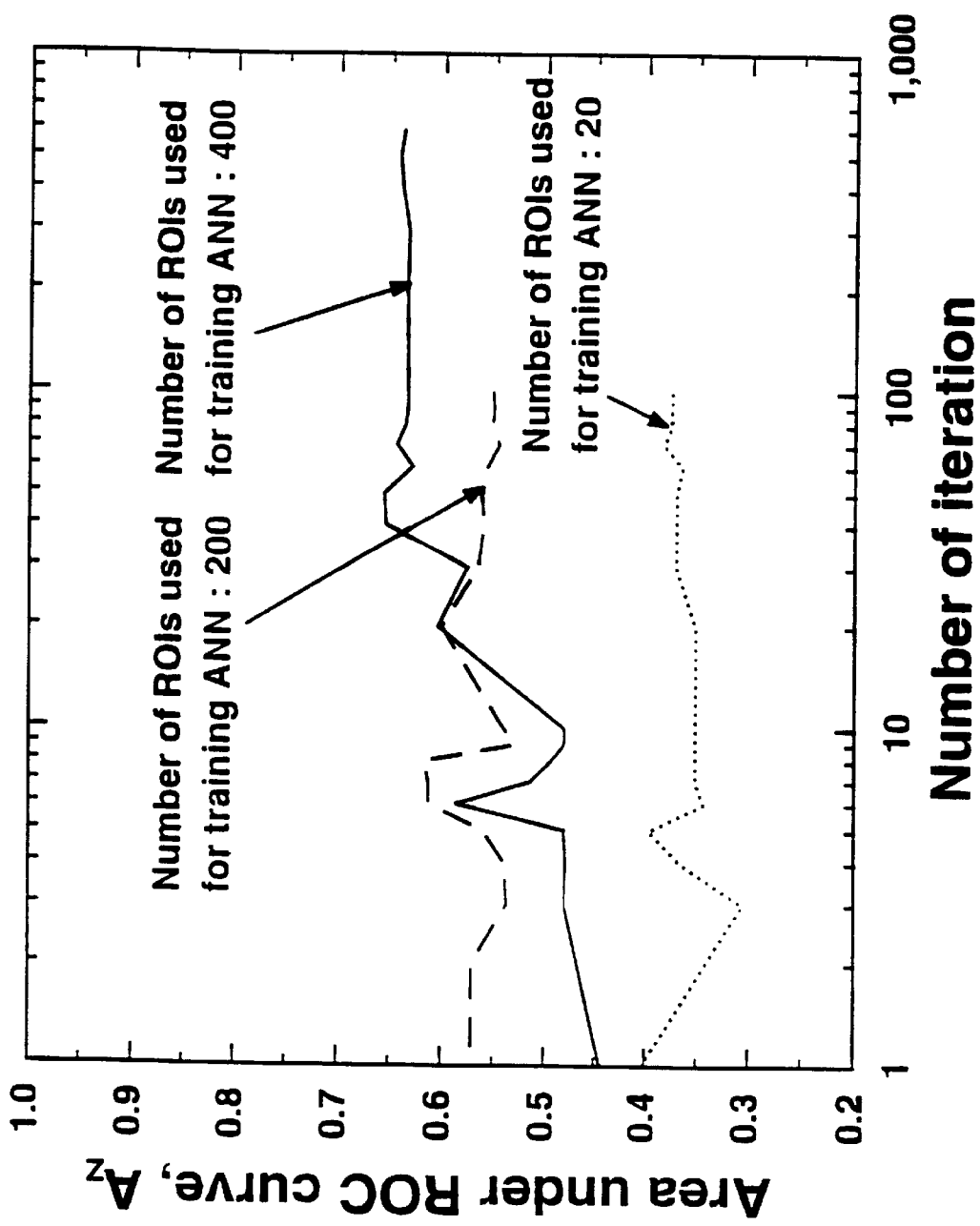
FIG. 7B is a graph showing the area under the ROC curve during a validation test of the ANNs trained according to FIG. 7A.

The present invention was compared with a different three layer, feed-forward ANN for distinguishing between normal and abnormal ROIs with interstitial infiltrates. The ANN consisted of 1,024 (32×32) input units, 128 hidden units, and 1 output unit. To train and test the ANN, 800 ROIs were randomly selected from 10 normal and 10 abnormal cases with severe interstitial lung disease, 400 ROIs for training and another 400 ROIs for testing of the ANN. The ANN was trained by trend corrected pixel values. On the consistency test, most of the ROIs were correctly identified by the ANN, as shown in FIG. 7A. However, according to the result of the validation test, the ROIs could not be recognized accurately in terms of normal and abnormal cases, as shown by low $A_z$ values in FIG. 7B. It seems that the results indicate that the number of training data sets was not adequate for learning the statistical property of interstitial infiltrate patterns.

However, if the number of training ROIs is increased, the computational time for training the ANN with a large number of input units will become extremely long, and thus it becomes impractical to use the ANN.

On the contrary, the present invention uses one-dimensional data, i.e., horizontal profiles; which can be used easily for training of the ANN, instead of all pixel data in ROIs. The present invention provides an increase in classification rate by training the system after reducing the amount of sub-optimal or contaminated training data. In order to investigate the effect of the reduction of the contaminated training data, three sets of ROIs are randomly selected from 10 normal and 10 abnormal cases with several interstitial infiltrates. Two sets were used for training and testing of the $1^{st}$ ANN, and the third set was used for validation test. The $1^{st}$ ANN was trained initially with the first training data set. Then, for testing, the second set was applied to the trained $1^{st}$ ANN, and subsequently, eliminated the horizontal profiles in the second data set which provided either large output values from the $1^{st}$ ANN for normal horizontal profiles or small output values for abnormal profiles. The fraction of the number of profiles eliminated varied from 25% to 75%.

After the elimination of the contaminated profiles, the $1^{st}$ ANN was retrained by the "non-contaminated" profiles in the second data set. Although the validation test data also include some contaminated horizontal profiles, the contaminated horizontal profiles were not eliminated for final testing in the validation test. Had the contaminated horizontal profiles been eliminated from the testing data, the classification performance would have been greatly improved. However, the improved performance obtained only with "non-contaminated" testing data would not be applicable to actual chest images, because chest images contain generally "contaminated" data.

Figure 8B:
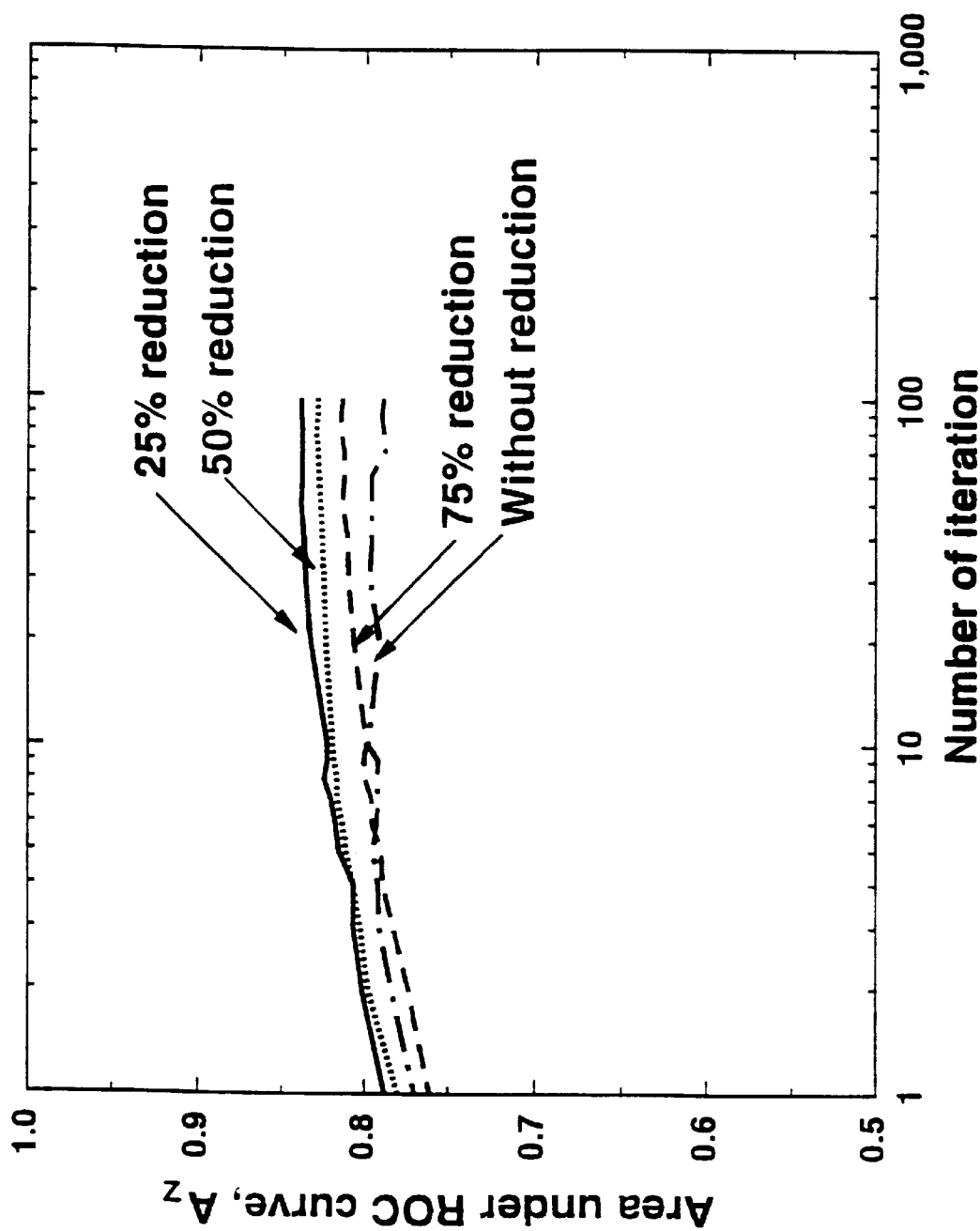
FIG. 8B is a graph showing the effect of the reduction of training data to avoid contamination on validation test results.

The results of the consistency test and the validation test with and without elimination of some contaminated training data are shown in FIGS. 8A and 8B, respectively. The graph of FIG. 8A indicates that, even by the consistency test, many horizontal profiles would not be correctly identified if some contaminated components in the training data were not eliminated. Clearly, the performance of the consistency test increases with the reduction of contaminated training data; however, in the validation test, the best performance was obtained when 25% of the training data were eliminated. When 75% of the training data were eliminated, the performance decreased slightly. This is probably because only obvious patterns would remain in the training data sets after the 75% removal, and thus the ANN would not be trained adequately because of the homogeneity of training data.

Figure 9:
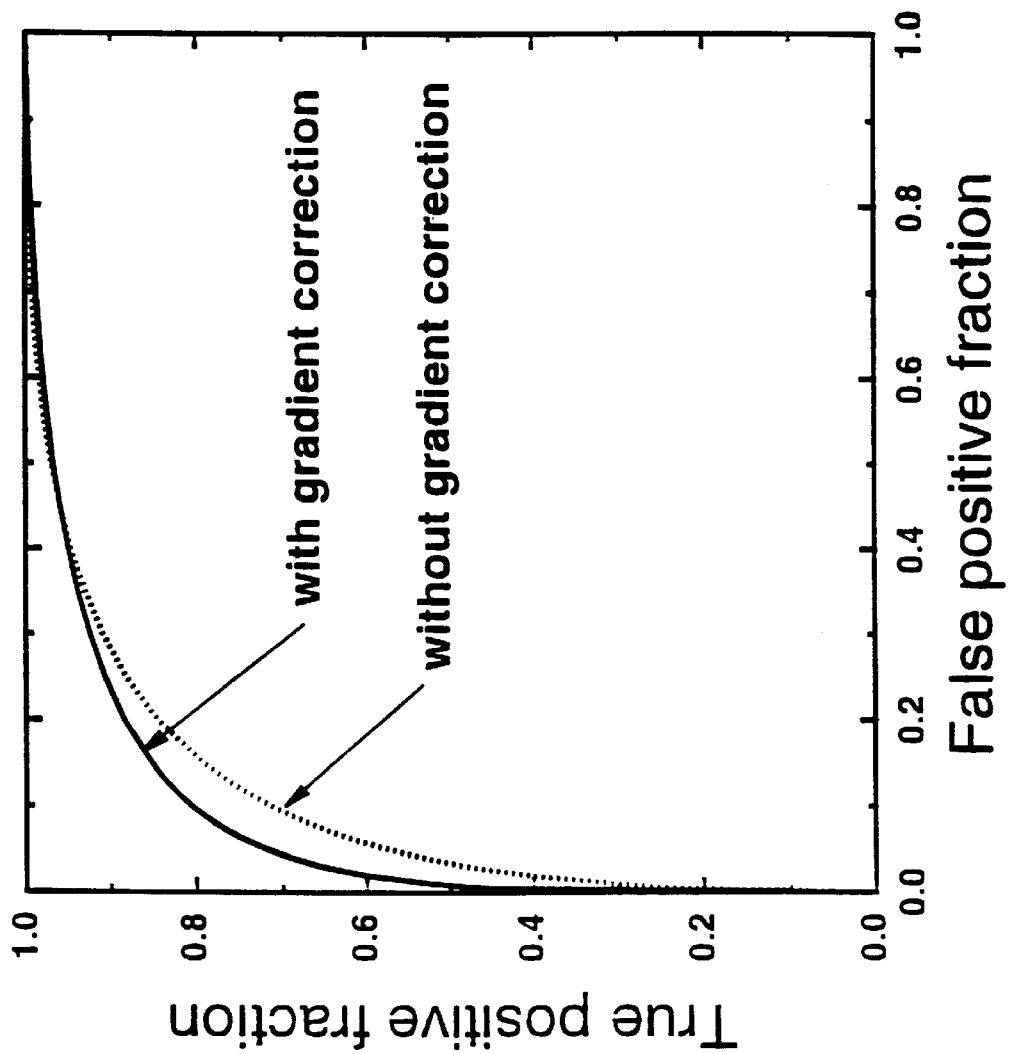
FIG. 9 is a graph showing a comparison of ROC curves with and without film gradient correction.

In addition, the present invention addresses problems caused by the scanning process of the radiograph. The ANN scheme tends to provide a number of false positive ROIs at high optical densities and also a number of false negative ROIs at low optical densities in digitized radiographs. These results are caused by the optical density dependence of the film gradient. Therefore, we employed an optical density correction technique by using a gradient curve of the OC film used. This technique is described in "Computer-aided diagnosis for interstitial infiltrate in chest radiographs: optical-density dependence of texture measures," Med. Phys. 22: 1515–1522 (1995), incorporated herein by reference, by J. Morishita, K. Doi, S. Katsuragawa, L. Monnier-Cholley, H. MacMahon. With this correction method, pixel values which are approximately proportional to the optical density are divided by the gradient of the film. The ROC curves with and without optical density correction are shown in FIG. 9. The $A_z$ values with and without the density correction are 0.928 and 0.905, respectively. The overall performance with and without 7the density correction was evaluated by use of four independent data sets. The average $A_z$ values with and without the density correction were 0.934±0.004 and 0.906±0.021, respectively. Therefore, the performance of the ANN scheme improves considerably by applying the optical density correction technique.

Figure 10B:
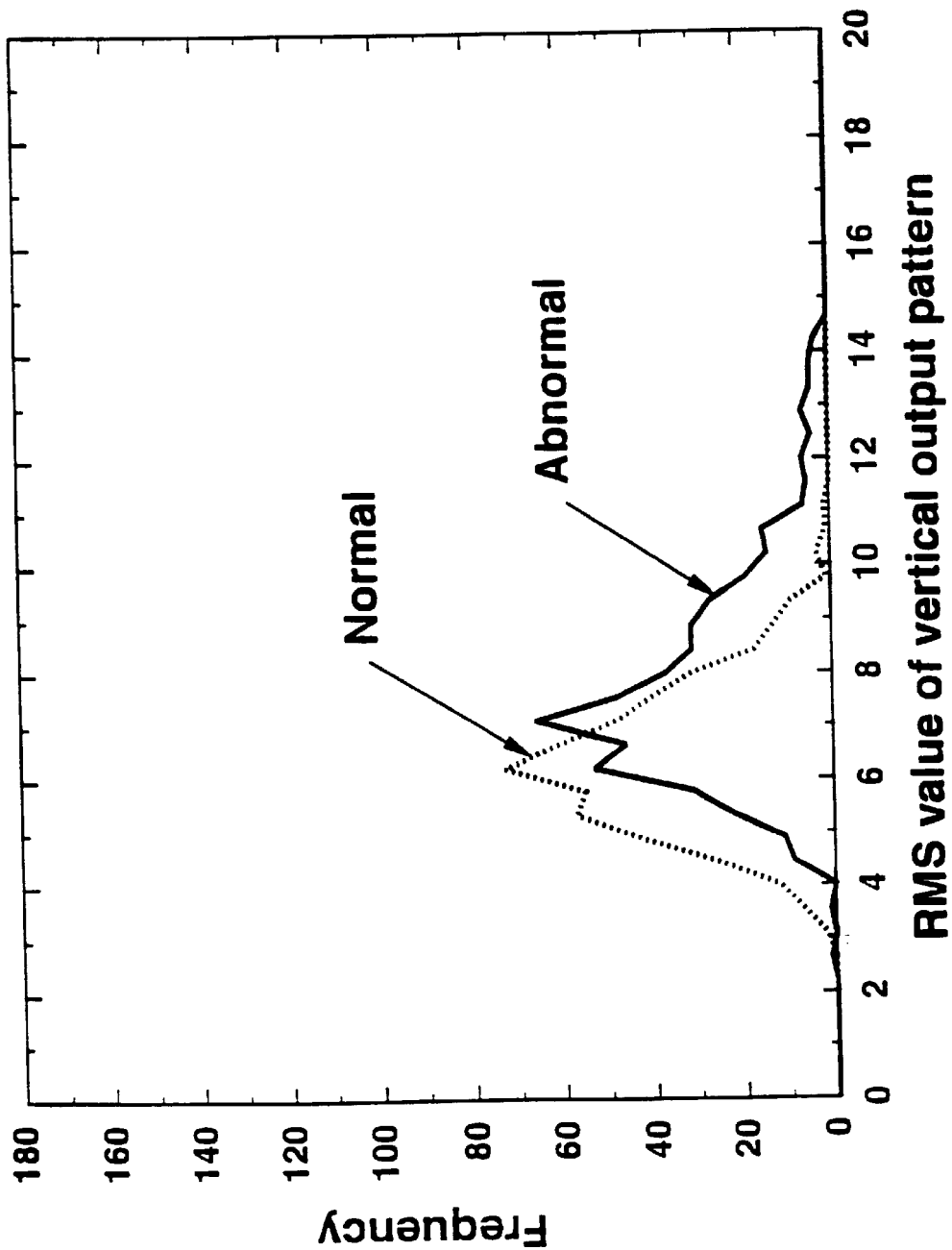
FIG. 10B is a histogram showing RMS values of each ROI using 1,000 ROIs.
Figure 11:
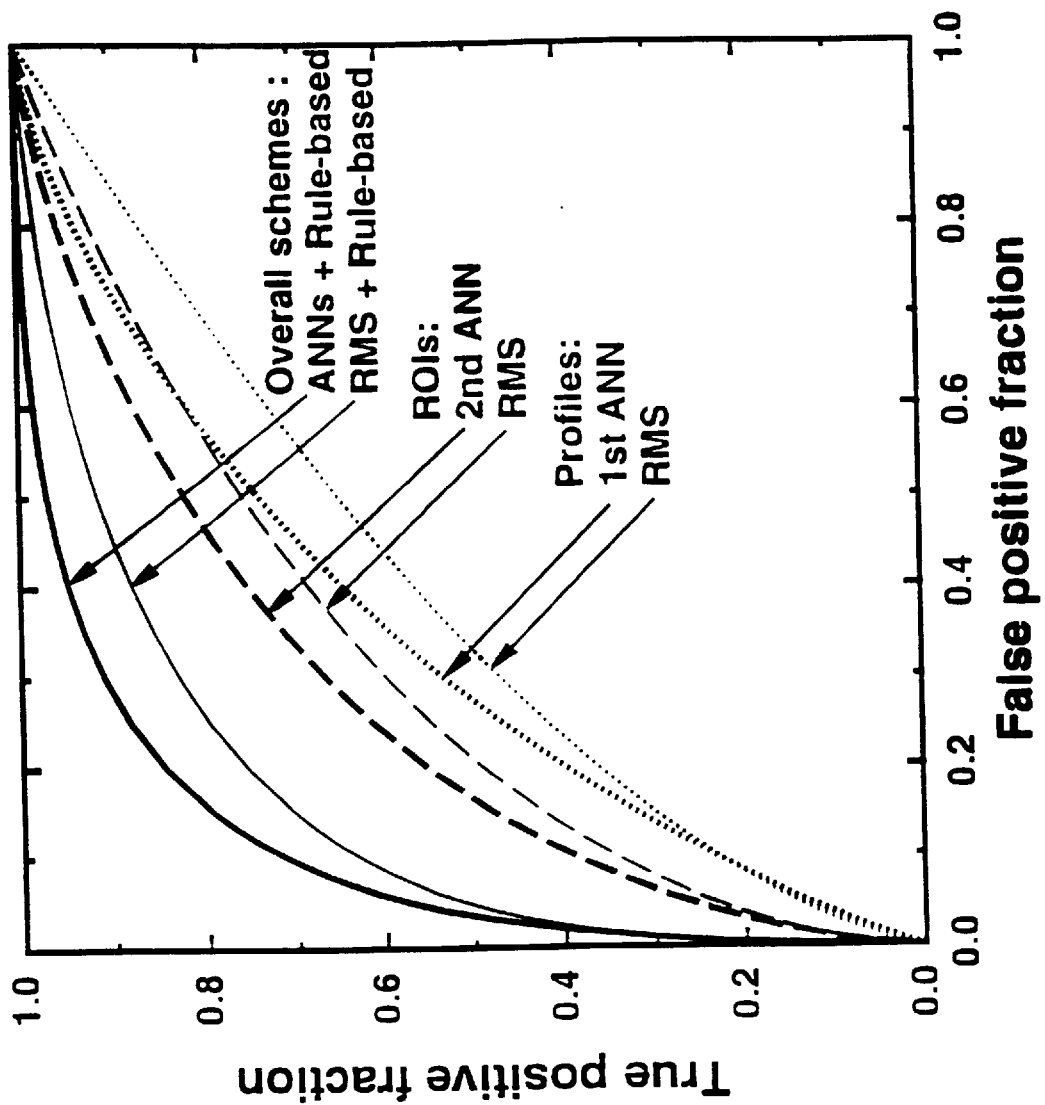
FIG. 11 is a graph showing a comparison of ROC curves between the ANN method and the rule-based method by use of RMS values.

As we described above, the RMS values of abnormal profiles are generally greater than and different from those of normal profiles. Therefore, one may assume that the $1^{st}$ ANN could have learned only the difference in the RMS values of the horizontal profiles between normal and abnormal patterns. However, it is possible that the $1^{st}$ ANN has learned the difference between the normal and abnormal patterns in terms of more than the RMS value, namely, some other statistical property associated with patterns of interstitial infiltrates. In order to examine this assumption, the performance by use of the RMS values of the horizontal profiles alone for distinction between normal and abnormal cases was determined. FIG. 10A is a histogram showing the frequencies of occurrence of the RMS values for normal and abnormal horizontal profiles. Since the two histograms were widely distributed and largely overlap, the ROC curve obtained from the values alone was very low, as shown by a short dotted line in FIG. 11, and was below the ROC curve obtained from the $1^{st}$ ANN. FIG. 10B is a histogram showing the frequenciews of occurrence of the RMS values for normal and abnormal ROIs, which partially overlap. The ROC curve obtained from the RMS values for ROIs was less than that obtained from the $2^{nd}$ ANN, as shown by a thin dashed line in FIG. 11. For the overall performance, the ROC curve obtained with the ANN scheme is clearly greater than that obtained with the rule-based method by use of RMS values. This seems to indicate that the ANN can learn some statistical properties of normal and abnormal patterns caused by interstitial infiltrates.

For the background trend correction, two different methods were investigated. One of these is the use of one-dimensional fitting for each horizontal profile, and the other is two-dimensional fitting for each ROI. Since, there was no significant difference between the results, two-dimensional background trend correction was used.

The effects of using vertical profiles instead of horizontal profiles for the training and testing of the $1^{st}$ ANN was assessed. The $1^{st}$ ANN and the $2^{nd}$ ANN contained the same structure as that used in the original scheme. The $2^{nd}$ ANN was trained by the outputs from the $1^{st}$ ANN for each ROI. The $A_z$ value of the overall scheme based on vertical profiles for distinguishing between normal and abnormal cases was 0.935. In addition, the effects of using rectangular segments (an 8×4 matrix), rather than horizontal and vertical profiles, for the training and testing of the $1^{st}$ ANN was also assessed. Since each ROI includes 32 segments the number of outputs from the $1^{st}$ ANN is 32 for each ROI. The $2^{nd}$ ANN was trained by the outputs from the $1^{st}$ ANN. The Az value based on rectangular segments was 0.925. In light of the fact that the $A_z$ value of the original scheme based on horizontal profiles was 0.928, there was no significant difference among the three overall performances based on horizontal profiles, vertical profiles, or rectangular segments.

The effect of varying the number of hidden units for the $1^{st}$ ANN and the $2^{nd}$ ANN by varying the number from 12 to 36 was investigated. The contaminated data for both training and testing were eliminated for this study. For the $1^{st}$ ANN, the $A_z$ value was increased from 0.890 to 0.930 as the number of hidden units was increased; however, the performance was saturated with more than 24 hidden units. For evaluation of the effect of the number of the hidden units for the $2^{nd}$ ANN, the training data and the testing data were produced by the $1^{st}$ ANN with 16 hidden units. There was no significant difference between the performance for the $2^{nd}$ ANN with different numbers of hidden units. The overall performance was evaluated by using the ANNs with 24 hidden units. The $A_z$ value was 0.928 which was the same as that obtained with the original scheme by using 16 hidden units.

Figure 12:
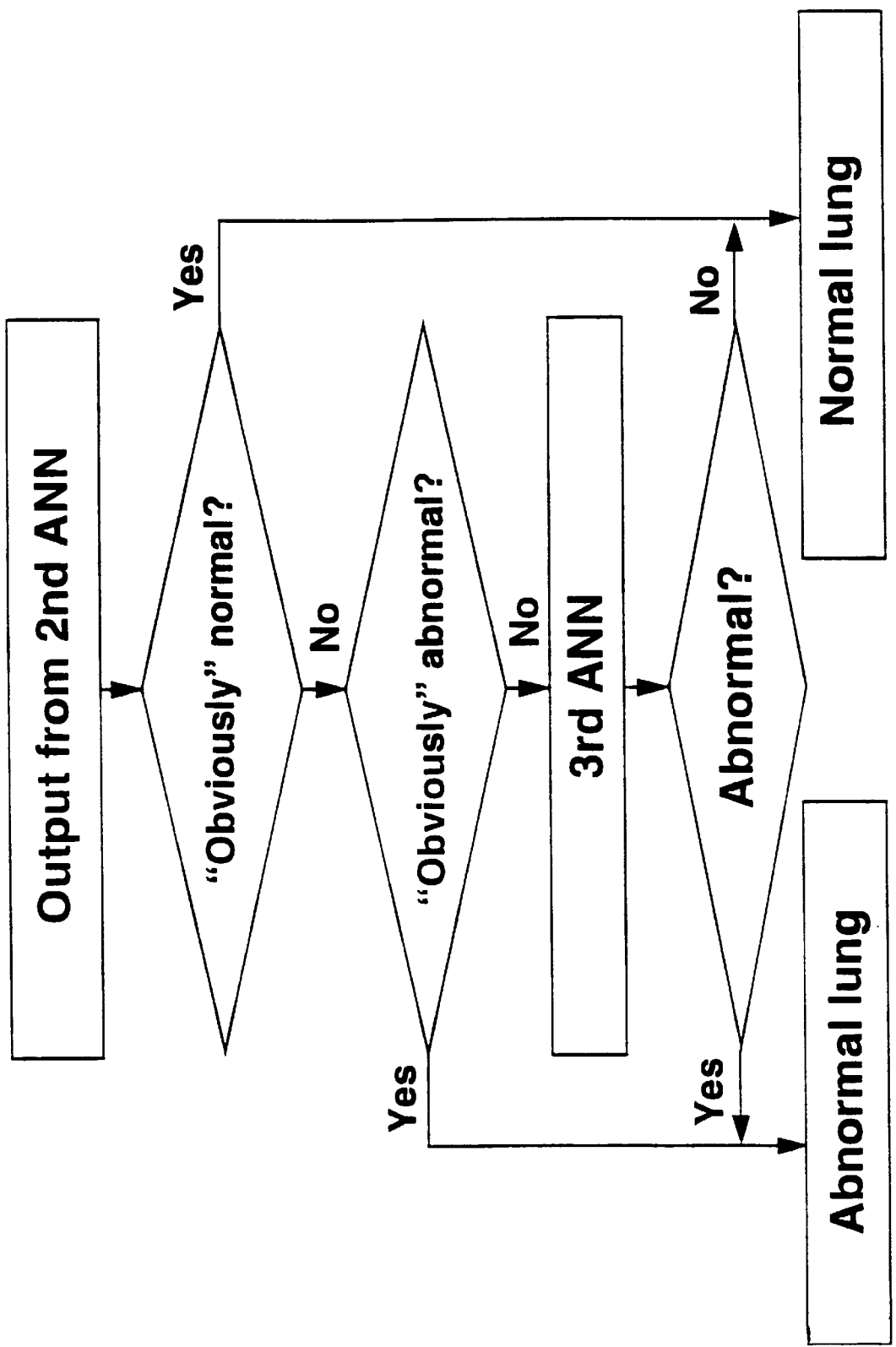
FIG. 12 is a flowchart showing the classification scheme of rule-based plus ANN method.
Figure 13A:
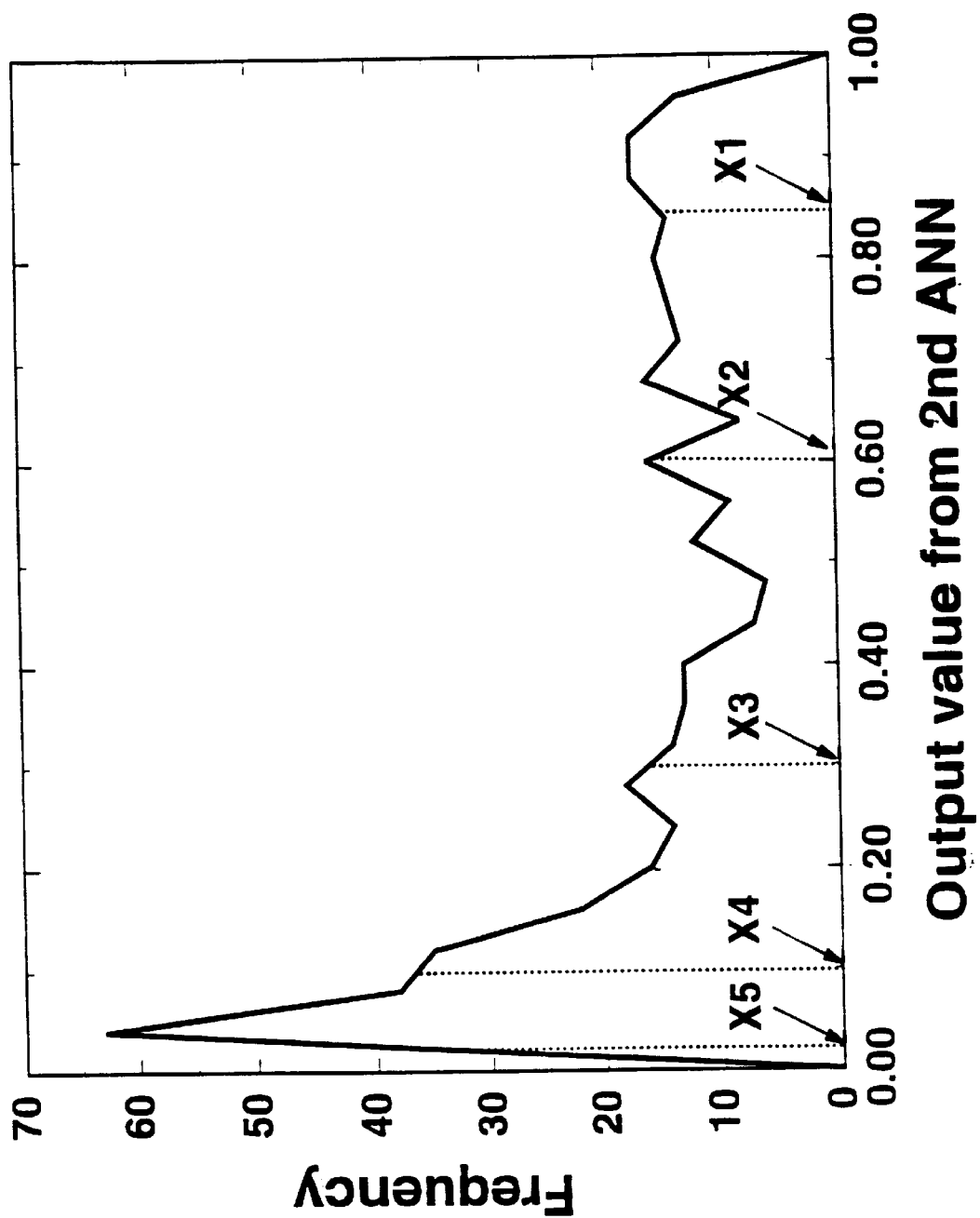
FIG. 13A is a histogram showing the frequency of the output values obtained from the $2^{nd}$ ANN from a normal chest radiograph.
Figure 13B:
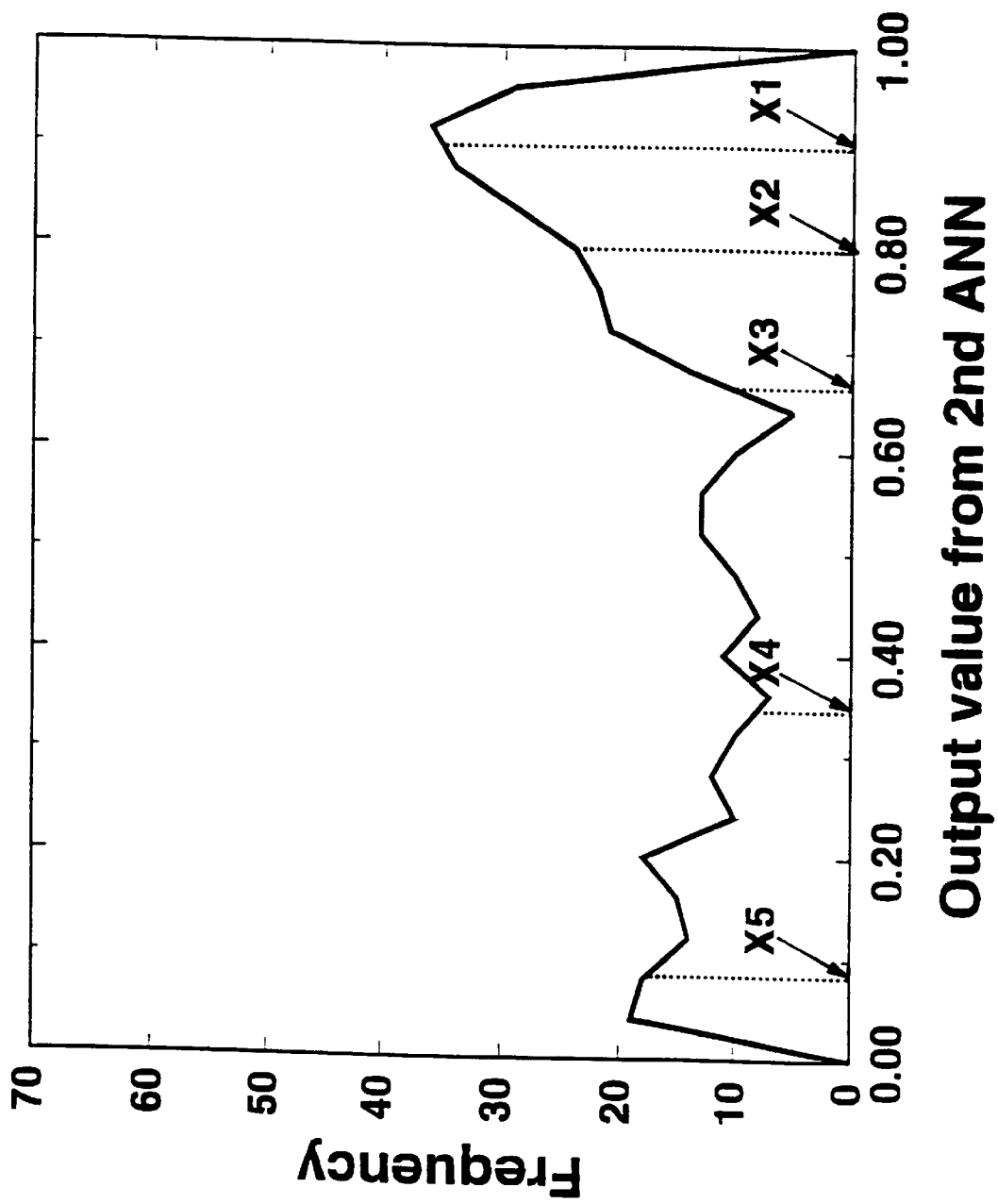
FIG. 13B is a histogram showing the frequency of the output values obtained from the $2^{nd}$ ANN from an abnormal chest radiograph with interstitial infiltrates, where X1–X5 show the input data selected for the $3^{rd}$ ANN.
Figure 14:
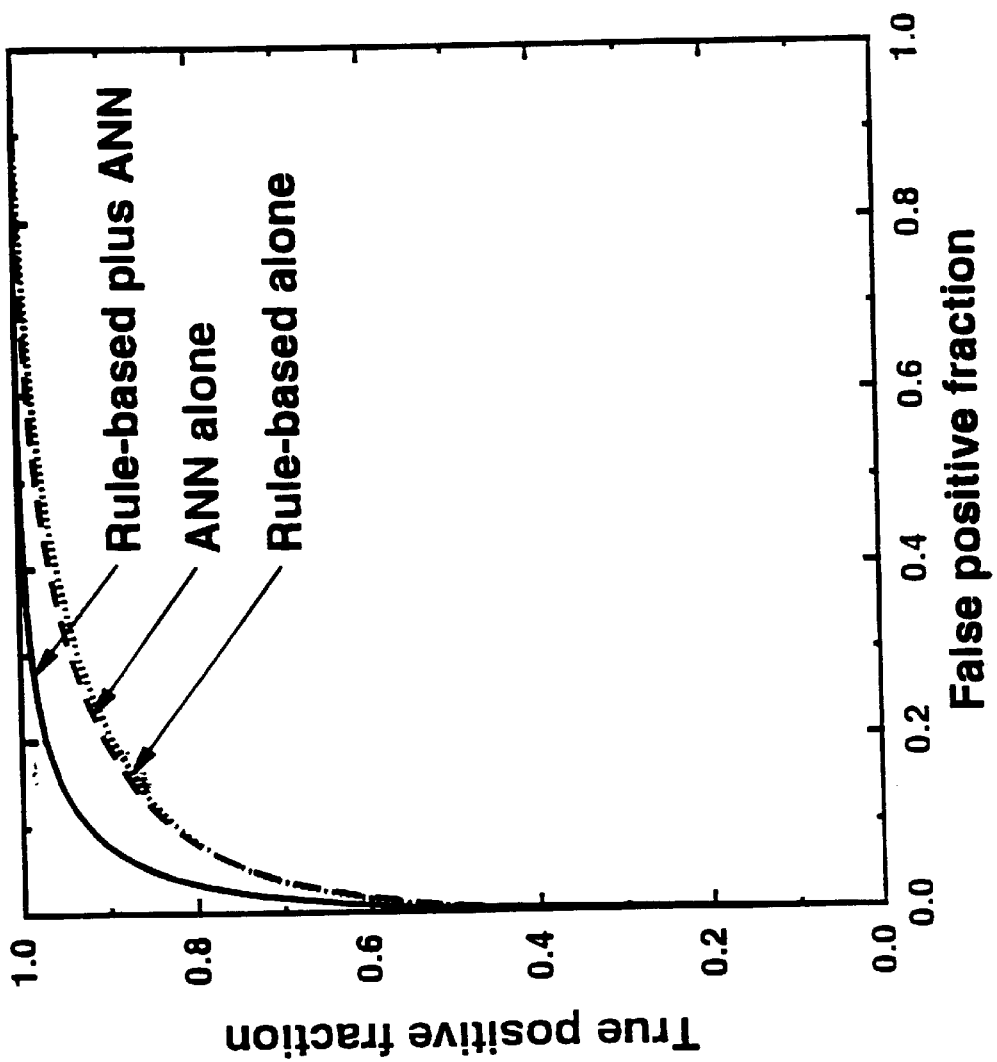
FIG. 14 is a graph showing a comparison of ROC curves between the rule-based classification and the rule-based plus ANN classification method.

For the overall classification of the results for each chest image, a rule-based method plus the ANN method was used. The flowchart describing the process is shown in FIG. 12. First, the rule-based method is employed for determination of "clearly" normal and "clearly" abnormal lungs. If the ratio of the number of abnormal ROIs to the total number of ROIs in the chest image is below the minimum "abnormal' ratio that can be obtained from all abnormal cases in a training data set, the chest image is classified as "clearly" normal. On the other hand, the chest image is classified as "clearly" abnormal, if the ratio is above the maximum "normal" ratio that can be obtained from all normal cases in the trained data set. Then, the remaining chest images are classified by applying the $3^{rd}$ ANN, which consists 5 input units, 3 hidden units, and 1 output unit. The input data for the $3^{rd}$ ANN are selected from a histogram of the output values from the $2^{nd}$ ANN for each chest image. FIGS. 13A and 13B are histograms showing the frequencies of occurrence of the output values for a normal case and an abnormal case, respectively. Five input values (X1 to X5) are selected from the corresponding output values from the $2^{nd}$ ANN as shown on the histogram of FIG. 13A. The output value from the $3^{rd}$ ANN ranges from 0 (normal) to 1 (abnormal). The average $A_z$ value by use of the rule-based plus ANN classification scheme was greatly improved from 0.934±0.004 to 0.972±0.008, as shown in FIG. 14. However, when the $3^{rd}$ ANN alone was applied to the overall classification without removal of obvious case by the rule-based method, the $A_z$ values was 0.938±0.002, which was quite low and comparable to that obtained with the rule-based classification scheme.

The effect of different input values to the 3rd ANN were examined with respect to the overall performances. FIGS. 15A and 15B show input values to the 3rd ANN which are derived from histograms of the output values from the 2nd ANN for a normal case and an abnormal case, respectively. Ten input values correspond to the ten frequency values at ten bins from 0–0.1 to 0.9–1.0. These ten input values represent more closely the distribution of the histogram. Ten input units are preferably employed for the 3rd ANN.

Figure 16:
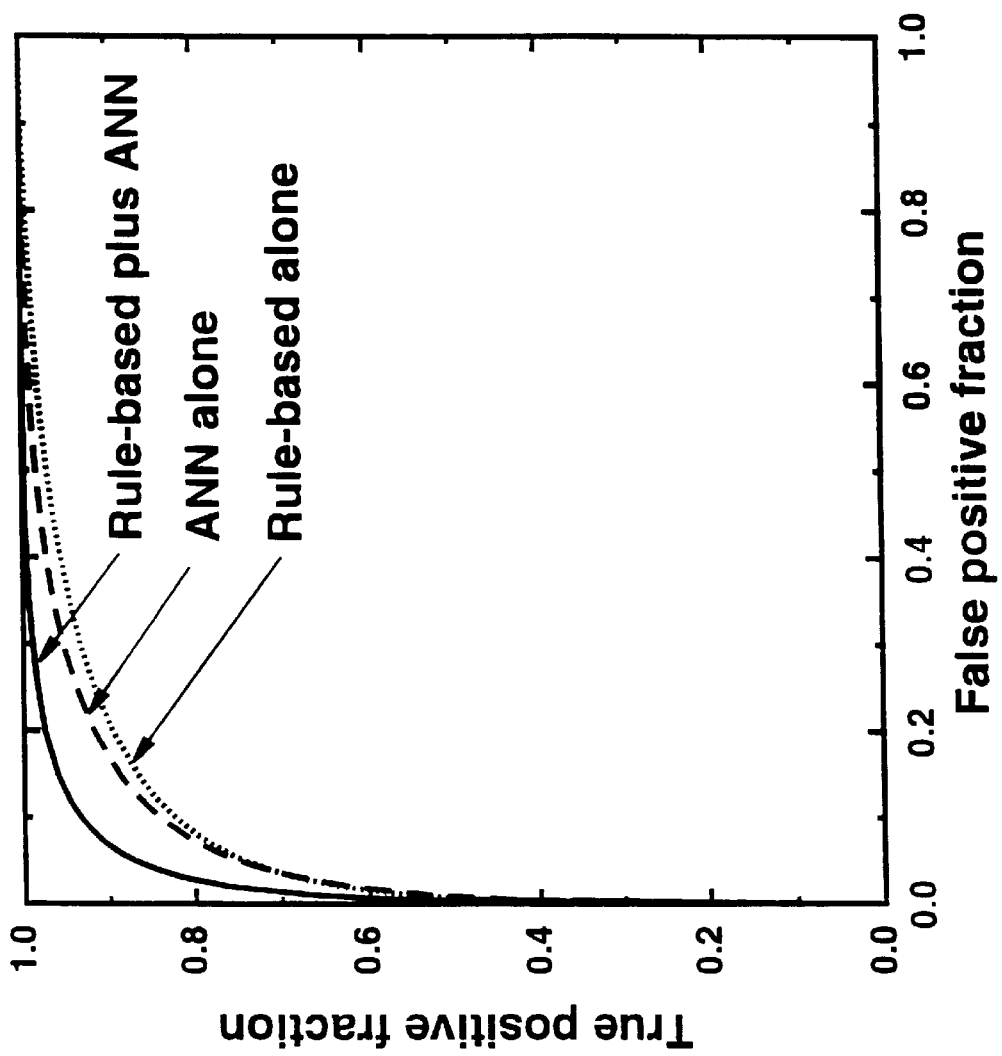
FIG. 16 is a comparison of ROC curves between the ANN method, the rule-based method, and the rule-based method plus ANN method.

The comparison of overall performances of the three classification methods, when ten input data are used for the 3rd ANN, is shown in FIG. 16 and the $A_z$ values obtained from ROC curves are summarized in Table 1. The sensitivities at a specificity of 90% obtained with the three classification methods are shown in Table 2.

TABLE 1

Overall performance (Az values) obtained with three classification methods using 10 inputs for the 3rd ANN

| | |
|---|---|
| Rule-based alone | 0.934 ± 0.004 |
| ANN alone | 0.945 ± 0.002 |
| Rule-based + ANN | 0.974 ± 0.010 |

TABLE 2

Sensitivity at a specificity of 90% obtained with three classification methods using 10 inputs for the 3rd ANN

| | |
|---|---|
| Rule-based alone | 78.85 ± 1.86% |
| ANN alone | 83.13 ± 1.10% |
| Rule-based + ANN | 93.20 ± 3.85% |

It is apparent that the rule-based plus ANN classification method was the best method and was slightly improved by using ten input values from the histogram, as compared with the result obtained by using five input values. The ANN classification method was also improved when the ten input values was employed for the 3rd ANN.

Figure 17:
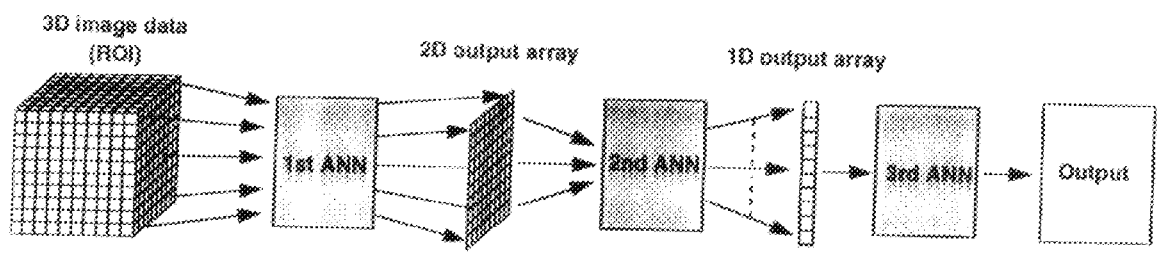
FIG. 17 is a schematic illustration of a system for analyzing three-dimensional images in a region of interests.

This scheme can be applied to analyze three-dimensional (3D) image data obtained from a medical imaging device such as computed tomography (CT), magnetic resonance imaging (MRI) and ultrasonography for quantitative analysis of texture patterns. FIG. 17 shows the overall scheme for the ANN analysis on one ROI obtained from 3-D digital image. A cube on the left represents a 3D array of pixel (or voxel) values in a selected ROI, where the matrix size may be 32×32×32. A different matrix size can be used depending on the size of normal and abnormal areas to be examined. A profile of pixel values along one direction in the cube such as horizontal, lateral or vertical profile can be entered to the first ANN for training (or testing) in the same way as that applied to the two-dimensional image data obtained from digital chest images, as described earlier. In this way, the system is actually implemented as a tree of neural networks with a larger number of strips being processed at a higher order (e.g., when converting from 3D data to 2D data) than at a lower order (e.g., when converting from 2D data to 1D data). Each neural network can therefore be thought of as a level of one-dimensional neural networks (i.e., only owrking with data from a strip of the image in one direction). Each one-dimensional neural network in a level is assigned the same neural network weighting parameters after training. In a parallel implementation of the present invention, the one-dimensional neural networks of each level would simultaneously receive their corresponding speed of classification compared to using a single one-dimensional neural network at each level and applying the data sequentially.

For a given 3D ROI, all (32×32) of horizontal profiles are entered to the input unit of the first ANN for initial distinction between normal and abnormal patterns caused by diseases such as interstitial infiltrates. The output pattern for this initial 3D image data results in a 2D array (32×32), which is similar to a 2D ROI image obtained from digital chest image.

For the second ANN, one-dimensional (1D) profile from this 2D array is used as input in a way similar to the horizontal profile obtained from the ROI of a chest image. The output from the 2nd ANN provides a set of 32 values corresponding to 32 profiles included in the 2D array of the output values obtained from the 1st ANN. The 32 output values are entered to the 3rd ANN for final distinction between normal and abnormal ROI of 3D digital image data selected from CT, MRI or ultrasonography.

The structures of three ANNs can have the same structure as those described for ANNs on chest images, namely, 32 input units, 16 hidden units and one output unit. The number of hidden units can be changed from 12 to 24. In addition, different number of input units can be used when a different number of pixels are included in the initial profile and also a different number of output patterns may be selected for entry to the subsequent ANN. The training of these ANNs are also made in the same way as that used for training on the ANN scheme for chest images, namely, by providing 0 and 1 to normal and abnormal ROI, respectively.

Since our ANN scheme can learn some statistical properties of image data on a selected ROI, this method can be applied to perform segmentation of image data such as distinction of different organs such as the liver, kidney, pancreas, spleen, blood vessels, lungs, heart, soft tissues and bones as well as distinction of normals and abnormals such as tumors and metastasises in CT, MRI and ultrasonography. Segmented 3D image data can be used to identify each organ for 3D visualization of each organ separately or with different colors assigned to different organs for display purposes on a color monitor.

Segmentation of 3D image data can be performed by applying a 3D grid over a 3D image. The 3D grid may contain a volume element of 32×32×32 matrix, and thus an original 3D image with 128×1,024×1,024 matrix can be broken to 4,096 (=4×32×32) volume elements. If a volume element is 8×8×8 matrix, then the total number of volume elements becomes 262,144 (=16×128×128), which is very large, but the segmentation can be done with a small volume element, thus yielding more accurate segmentation in terms of the boundaries between different organs. Generally, a large volume element is useful for detection of subtle, low-contrast abnormalities, whereas a small volume element is preferred for accurate segmentation of boundaries.

Training of our ANN scheme for segmentation can be made by using image data with a known organ individually such as the liver. All of the three ANNs are trained by providing the teacher data of 1 and 0 for the liver and other structures, respectively. The trained ANNs for the liver is thus useful in distinguishing between the liver and other structures. Training of other organs can be made in a similar way on each of separate ANN schemes. Once all of the ANN schemes are trained for all of the organs and structures required for segmentation, a clinical 3D image data for study can be analyzed by a set of the trained ANN schemes sequentially or in parallel for segmentation of the organs. The output values from each ANN scheme are then subjected to thresholding using a set of preselected threshold values for each organ. A volume element yielding the output value above the preselected threshold value is considered to be a part of the organ with the trained ANN scheme used. Segmentation is completed by grouping all of volume elements to each organ.

When real-time ultrasound images are obtained, 3D image data are generated sequentially on time, thus producing four-dimensional (4D) image data. Fluoroscopic CT system and some MRI units also produces 4D image data. Our scheme of analyzing texture patterns can be applied to these 4D image data. For analysis of 4D image data, four ANNs are applied sequentially by expanding the scheme illustrated for analysis of 3D image data shown in FIG. 17.

Two different approaches can be implemented. One approach is to analyze first each of all 3D image data acquired at different times by the scheme shown in FIG. 17. This initial analysis produces a number of output values which are then analyzed by the 4th ANN to distinguish between normal and abnormal regions. Another approach is first to analyze time-sequential image data at each of all 3D pixel locations by using an initial ANN, the number of input units for which is equal to the number of image data acquired in time domain. The output values from this initial ANN are assigned to each of all 3D pixel locations. Then the 3D output values are analyzed by the 3D scheme shown in FIG. 17.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. An apparatus for generating a partial diagnosis based on image data, the apparatus comprising:
   a plurality of one-dimensional neural networks connected in a tree of levels, the tree of levels comprising
   a) a plurality of first-level one-dimensional neural networks receiving strips of two-dimensional image data and outputting one-dimensional image data, and
   b) a second-level one-dimensional neural network receiving the one-dimensional data output from the plurality of first-level networks and outputting a partial diagnosis.

2. The apparatus as claimed in claim 1, further comprising:
   an evaluator for pre-classifying a plurality of images into a corresponding complete diagnosis of one of normal, abnormal, and undecided; and
   a classification neural network for receiving statistics on the images classified as undecided and for determining a corresponding complete diagnosis of one of normal and abnormal.

3. The apparatus as claimed in claim 2, wherein the evaluator comprises:
   a normal evaluator for determining that the complete diagnosis is normal if a ratio is below a minimum value, the ratio obtained by dividing a number of images which are abnormal by a number of the plurality of images; and
   an abnormal evaluator for determining that the complete diagnosis is abnormal if the ratio is above a maximum value.

4. The apparatus as claimed in claim 1, wherein each neural network of the plurality of one-dimensional neural networks comprises:
   a first layer including 32 input units;
   a second layer including 16 hidden units; and
   a third layer including one output unit.

5. The apparatus as claimed in claim 1, further comprising:
   means for training the plurality of one-dimensional neural networks on a level-by-level basis using plural training iterations until an area under an ROC curve is greater than a minimum value.

6. The apparatus as claimed in claim 1, further comprising:
   a pre-filter for pre-filtering raw image data to create the image data.

7. The apparatus as claimed in claim 6, wherein the pre-filter comprises an optical density correction device for performing an optical density correction using a gradient curve of a medium from which the image data was generated.

8. The apparatus as claimed in claim 1, wherein the image data is initially three-dimensional image data, the apparatus further comprising:
   a plurality of third-level one-dimensional neural networks connected to the tree of levels, wherein the plurality of third-level one-dimensional neural networks receive strips of the three-dimensional image data and output the two-dimensional image data to the plurality of first-level one-dimensional neural networks.

9. The apparatus as claimed in claim 1, wherein the image data is initially at least three-dimensional image data, the apparatus further comprising:

a plurality of higher-levels of one-dimensional neural networks connected to the tree of levels, wherein the plurality of higher-levels of one-dimensional neural networks receive strips of the at least three-dimensional image data and output the two-dimensional image data to the plurality of first-level one-dimensional neural networks.

10. A method of generating a partial diagnosis based on image data, the method comprising the steps of:

applying strips of two-dimensional image data to a plurality of first-level one-dimensional neural networks included in a plurality of one-dimensional neural networks connected in a tree of levels;

outputting one-dimensional image data from the plurality of first-level one-dimensional neural networks;

receiving the one-dimensional image data at a second-level one dimensional neural network of the plurality of one-dimensional neural networks connected in a tree of levels; and outputting a partial diagnosis from the second-level one-dimensional neural network of the plurality of one-dimensional neural networks.

11. The method as claimed in claim 10, further comprising the steps of:

pre-classifying a plurality of images into a corresponding complete diagnosis of one of normal, abnormal, and undecided;

applying to a classification network statistics of the images classified as undecided; and determining, using the classification neural network, a corresponding complete diagnosis of one of normal and abnormal for the images classified as undecided.

12. The method as claimed in claim 11, wherein the step of pre-classifying comprises:

calculating a ratio by dividing a number of images which are abnormal by a number of the plurality of images;

determining that the complete diagnosis is normal if the ratio is below a minimum value; and determining that the complete diagnosis is abnormal if the ratio is above a maximum value.

13. The method as claimed in claim 10, wherein the step of outputting one-dimensional image data comprises the steps of:

applying a strip of two-dimensional image data to a first layer including 32 input units;

applying outputs of the 32 input units to a second layer including 16 hidden units; and applying outputs of the 16 hidden units to a third layer including one output unit to produce one datum for the one-dimensional image data.

14. The method as claimed in claim 10, further comprising the step of:

training the plurality of one-dimensional neural networks on a level-by-level basis using plural training iterations until an area under an ROC curve is greater than a minimum value.

15. The method as claimed in claim 10, further comprising the step of:

pre-filtering raw image data to create the image data.

16. The method as claimed in claim 15, wherein the step of pre-filtering comprises performing an optical density correction using a gradient curve of a medium from which the image data was generated.

17. The method as claimed in claim 10, wherein the image data is initially three-dimensional image data, the method further comprising the steps of:

receiving strips of the three-dimensional image data at a plurality of third-level one-dimensional neural networks connected to the tree of levels; and outputting the two-dimensional image data to the plurality of first-level one-dimensional neural networks.

18. The method as claimed in claim 10, wherein the image data is initially at least three-dimensional image data, the method further comprising the steps of:

receiving strips of the at least three-dimensional image data at a plurality of higher-levels of one-dimensional neural networks connected to the tree of levels; and outputting, from the plurality of higher-levels of one-dimensional neural networks, the two-dimensional image data to the plurality of first-level one-dimensional neural networks.

19. A computer program product, comprising:

a computer storage medium and a computer program code mechanism embedded in the computer storage medium for causing a computer to generate a partial diagnosis based on image data, the computer program code mechanism comprising:

a first computer code device configured to implement a plurality of one-dimensional neural networks connected in a tree of levels, wherein the tree of levels includes a plurality of first-level one-dimensional neural networks and a second-level one-dimensional neural network;

a second computer code device configured to apply strips of two-dimensional image data to the plurality of first-level one-dimensional neural networks of the plurality of one-dimensional neural networks;

a third computer code device configured to output one-dimensional image data from the plurality of first-level one-dimensional neural networks to the second-level one-dimensional neural network; and a fourth computer code device configured to output a partial diagnosis based on the one-dimensional image data.

20. The computer program product as claimed in claim 19, further comprising:

a fifth computer code device configured to pre-classify a plurality of images into a corresponding complete diagnosis of one of normal, abnormal, and undecided;

a sixth computer code device configured as a classification neural network;

a seventh computer code device configured to apply to the classification network statistics of the images classified as undecided; and an eighth computer code device configured to classify an output of the classification neural network as a corresponding complete diagnosis of one of normal and abnormal for the images classified as undecided.

21. The computer program product as claimed in claim 20, wherein the fifth computer code device comprises:

a ninth computer code device configured to determine that the complete diagnosis is normal if a ratio is below a minimum value, the ratio obtained by dividing a number of images which are abnormal by a number of the plurality of images; and a tenth computer code device configured to determine that the complete diagnosis is abnormal if the ratio is above a maximum value.

22. The computer program product as claimed in claim 19, wherein the first computer code device comprises:

a fifth computer code device configured as a first layer including 32 input units;

a sixth computer code device configured as a second layer including 16 hidden units; and a seventh computer code device configured as a third layer including one output unit to produce one datum for the one-dimensional image data.

23. The computer program product as claimed in claim 19, further comprising:

a fifth computer code device configured to train the plurality of one-dimensional neural networks on a level-by-level basis using plural training iterations until an area under an ROC curve is greater than a minimum value.

24. The computer program product as claimed in claim 19, further comprising:

a fifth computer code device configured to pre-filter raw image data to create the image data.

25. The computer program product as claimed in claim 24, wherein the fifth computer code device is configured to perform an optical density correction using a gradient curve of a medium from which the image data was generated.

26. The computer program product as claimed in claim 19, wherein the image data is initially three-dimensional image data, the computer program product further comprising:

a fifth computer code device configured to receive strips of the three-dimensional image data at a plurality of third-level one-dimensional neural networks connected to the tree of levels; and a sixth computer code device configured to output the two-dimensional image data to the plurality of first-level one-dimensional neural networks.

27. The computer program product as claimed in claim 19, wherein the image data is initially at least three-dimensional image data, the computer program product further comprising:

a fifth computer code device configured to receive strips of the at least three-dimensional image data at a plurality of higher-levels of one-dimensional neural networks connected to the tree of levels; and a sixth computer code device configured to output, from the plurality of higher-level one-dimensional neural networks, the two-dimensional image data to the plurality of first-level one-dimensional neural networks.

* * * * *